(12) United States Patent
Yeh et al.

(10) Patent No.: US 8,119,684 B2
(45) Date of Patent: Feb. 21, 2012

(54) THIOPHENE DERIVATIVES FOR UP-REGULATING HLA-DM ACTIVITY

(75) Inventors: Li-An Yeh, Cary, NC (US); Gregory D. Cuny, Somerville, MA (US); Melissa Call, Boston, MA (US); Kai Wucherpfennig, Brookline, MA (US); Ross L. Stein, Cambridge, MA (US)

(73) Assignees: Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 954 days.

(21) Appl. No.: 10/585,216

(22) PCT Filed: Dec. 29, 2004

(86) PCT No.: PCT/US2004/043950
§ 371 (c)(1),
(2), (4) Date: Jan. 6, 2009

(87) PCT Pub. No.: WO2005/066152
PCT Pub. Date: Jul. 21, 2005

(65) Prior Publication Data
US 2010/0143404 A1 Jun. 10, 2010

Related U.S. Application Data

(60) Provisional application No. 60/533,720, filed on Dec. 30, 2003.

(51) Int. Cl.
*A61K 31/40* (2006.01)
(52) U.S. Cl. .................................................. 514/423
(58) Field of Classification Search ............ 514/423
See application file for complete search history.

(56) References Cited

U.S. PATENT DOCUMENTS

2002/0042428 A1 4/2002 Myers et al.
2003/0187002 A1 10/2003 Mortlock et al.

FOREIGN PATENT DOCUMENTS

| EP | 0 234 622 A1 | 9/1987 |
| EP | 0 273 602 A1 | 7/1988 |
| EP | 1 176 139 A1 | 1/2002 |
| WO | WO 99/55682 A1 | 11/1999 |
| WO | WO 03/006047 A2 | 1/2003 |

OTHER PUBLICATIONS

Curphey et al., Dianions of 3-oxodithioic acids: preparation and conversion to 3H-1, 2-dithiole-3-thiones. Tetrahedron Letters 2000;41:6977-6980.
Dolling et al., Synthese neuer ketendithioacetale aus n-cyanomethyl-2,2,n-trimethyl-propionamid, n-cyanomethyl-n-methyl-benzamid bzw. 4,4-dimethyl-3-oxo-pentannitril und schwefelkohlenstoff. Phosphorus, Sulfur, Silicon, Relat. Elem. 1994;86(1-4):129-137.
Singh et al., Bromination of a-aroylketene s,s-acetals: synthesis of novel a-aroyl-a-bromoketene s,s-acetals and their further synthetic transformations. Synthesis 1985;2:165-169.
Yamamoto et al., Intramolecular radical cyclization of ketene dithioacetals. Bull Chem Soc Jpn 1992;65(6):1550-1555.

*Primary Examiner* — Taofiq A Solola
(74) *Attorney, Agent, or Firm* — Wolf, Greenfield & Sacks, P.C.

(57) ABSTRACT

Compounds of formula (I), compositions, methods and kits are provided. The compounds and compositions may be particularly useful for modulating immunological responses. Formula (I) wherein, $R_1$ is alkyl, aryl, or heterocyclyl; $R_2$ is H, alkyl, aryl, heterocyclyl, $OR_3$ or $N(R_3)_2$, $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

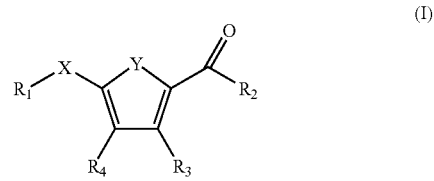

(I)

16 Claims, 10 Drawing Sheets

CALCULATE Km AND Vmax FROM INITIAL RATES

| BEST-FIT VALUES | F15 | DMSO |
|---|---|---|
| $V_{MAX}$ (x$10^{-8}$) | 0.07611 | 0.02521 |
| PEP | 1.000e-008 | 1.000e-008 |
| KM | 1.343e-006 | 1.055e-006 |
| Std. ERROR | | |
| VMAX | 0.004248 | 0.0005050 |
| KM | 2.340e-007 | 7.033e-008 |
| 95% CONFIDENCE INTERVALS | | |
| VMAX | 0.06710 TO 0.08512 | 0.02414 TO 0.02628 |
| KM | 8.465e-007 TO 1.839e-006 | 9.059e-007 TO 1.204e-006 |
| GOODNESS OF FIT | | |
| DEGREES OF FREEDOM | 16 | 16 |
| $R^2$ | 0.9269 | 0.9875 |

THIOPHENE DERIVATIVES FOR UP-REGULATING HLA-DM ACTIVITY

This application is a national stage filing under 35 U.S.C. §371 of PCT International application PCT/US2004/043950 designating the United States of America, and filed Dec. 29, 2004. This application claims the benefit under 35 U.S.C. §119(e) of U.S. provisional application Ser. No. 60/533,720, filed Dec. 30, 2003, the entire contents of which are hereby incorporated by reference.

BACKGROUND OF INVENTION

1. Field of Invention

The present invention relates to compounds and compositions for modulating immunological responses and, more specifically, to compounds and compositions for up-regulating HLA-DM activity. The invention also relates to assays and kits.

2. Discussion of Related Art

The invariant HLA-DM molecule in humans is involved in loading peptides onto MHC class II molecules. It is encoded in the MHC within a set of genes resembling MHC class II genes. A homologous protein in mice is called H-2M.

HLA-DM is a molecule that may act as a catalyst for peptide exchange by positively selecting peptides with a high affinity for MHC class II. In some instances, an increase or decrease in HLA-DM activity may be beneficial in disease treatment. For example, a subject exhibiting symptoms of, or predisposed to, certain autoimmune diseases may benefit from a decrease in HLA-DM activity. Alternatively, a subject exhibiting symptoms of, or a predisposition to, an infection or a cancer may benefit from increased HLA-DM activity. Likewise, a subject may benefit from an increase in HLA-DM activity in response to a disease that downregulates HLA-DM.

HLA-DM may also act as a peptide editor by positively selecting peptides having a high affinity for MHC class II. Acceleration of the catalytic exchange of peptides may increase high affinity peptides and/or decrease low affinity peptides displayed on the surface of antigen presenting cells. As it is believed that high affinity peptides are more immunogenic than are low affinity peptides, a change (e.g., an increase) in the ratio of high affinity to low affinity peptides may improve a subject's immune response to a pathogen.

It would be desirable to have compounds that could influence HLA-DM activity and, hence, the immune response.

SUMMARY OF INVENTION

According to one aspect of the invention, a compound is provided. The compound is of the following formula:

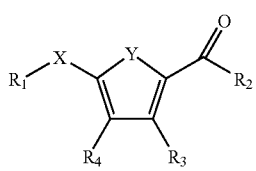

Formula I wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and Y is S.

In one embodiment, the compound is represented by the formula:

Compound F15

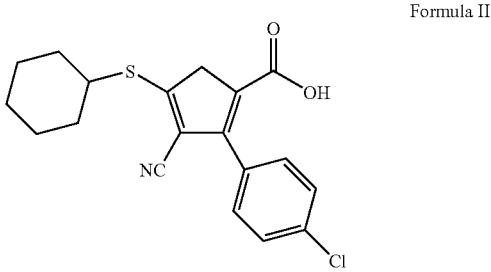

Formula II

According to another aspect of the invention, a pharmaceutical composition is provided. The pharmaceutical composition includes an effective amount of a compound of the formula:

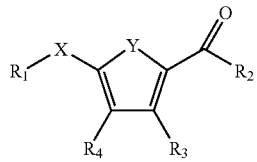

wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and Y is S, and a pharmaceutically acceptable carrier. The pharmaceutical composition can be sterile. It can optionally include any one or combination of a buffering agent, a chelating agent, a preservative or an isotonicity agent.

In one embodiment, the pharmaceutical composition further includes an anti-cancer agent. In some embodiments the anti-cancer agent is a cytotoxic agent. In other embodiments the anti-cancer agent is an antibody. In one embodiment, the pharmaceutical composition further includes an anti-pathogenic agent. In some embodiments, the anti-pathogenic agent is an anti-viral agent. In other embodiments, the anti-pathogenic agent is an anti-bacterial agent. In one embodiment, the pharmaceutical composition further contains an antigen. In some embodiments, the antigen is a cancer antigen. In other embodiments, the antigen is a viral antigen, a bacterial antigen, a fungal antigen or a parasitic antigen. The pharmaceutical composition also can further include, separate from or in addition to the antigen, an immunomodulatory agent. In some embodiments, the immunomodulatory agent is any one or more of an adjuvant, a hematopoietic cell stimulator, a cytokine, a growth factor, or an immunostimulatory oligonucleotide.

According to another aspect of the invention, a method is provided for modulating an immune response in a subject. The method involves administering to a subject in need of such immune modulation an amount of a compound of the formula:

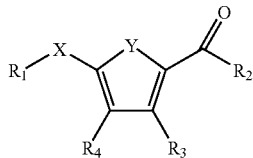

wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and
Y is S effective to modulate the subjects immune response to an antigen. In one embodiment, the immune response is modulated by enhancing the subject's immune response to the antigen. In one embodiment, the subject's immune response is modulated by increasing in the subject the number of high affinity antibodies to the antigen.

According to another aspect of the invention, a method is provided for treating a subject having or at risk of having a cancer expressing a cancer antigen. The method involves administering to the subject a therapeutically effective amount of the formula:

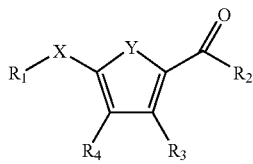

wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and
Y is S. In one embodiment, the cancer is selected from the group consisting of a leukemia, a melanoma, a renal cell carcinoma, a colon cancer, a liver cancer, a pancreatic cancer, and a lung cancer. In another embodiment, the cancer expresses MHC class II. In another embodiment, the cancer is a B-cell lymphoma. In another embodiment, the cancer is a refractory cancer. In one embodiment, the subject has had or is scheduled to have surgery, radiation treatment or chemotherapy.

In one embodiment, the method further involves administering to the subject a cancer antigen. The cancer antigen is in some embodiments a cancer antigen as described in detail below. In one embodiment, the invention further involves administering to the subject one or more immunomodulatory agents, with or without the antigen. Examples of immunomodulatory agents are an adjuvant, a hematopoietic cell stimulator, a cytokine, a growth factor or an immunostimulatory oligonucleotide.

In one embodiment, the method involves administering to the subject an anti-cancer agent. The anti-cancer agent in some embodiments is a cytotoxic agent and in other embodiments an antibody. Preferred anticancer agents are as described in detail below.

According to another aspect of the invention, a method is provided for treating a subject having or at risk of having an infectious disease. The method involves administering to the subject a therapeutically effective amount of a compound of the formula:

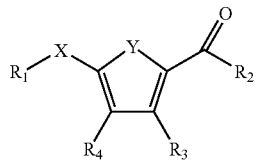

wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and
Y is S. The infectious disease can be a viral infection, a bacterial infection, a fungal infection or a parasitic infection. In one embodiment, the infectious disease is a chronic infection. In one embodiment the infectious disease is a chronic infection with HIV, Hepatitis C or tuberculosis. In one embodiment, the subject has a bacterial infection and further comprising administering to the subject an anti-bacterial agent. In one embodiment, the subject has a viral infection and further comprising administering to the subject an anti-viral agent. In one embodiment, the subject has a fungal infection and further comprising administering to the subject an anti-fungal agent. In one embodiment, the subject has a parasitic infection and further comprising administering to the subject an anti-parasitic agent.

In one embodiment, the method further involves administering to the subject a pathogen antigen. The antigen can be, for example, a viral antigen, a bacterial antigen, a fungal antigen, or a parasitic antigen. In some embodiments, the antigen is among those described specifically below. In one embodiment, the invention further involves administering to the subject one or more immunomodulatory agents, with or without the antigen. Examples of immunomodulatory agents are an adjuvant, a hematopoietic cell stimulator, a cytokine, a growth factor or an immunostimulatory oligonucleotide.

In one embodiment, the method involves administering to the subject an anti-cancer agent. The anti-cancer agent in some embodiments is a cytotoxic agent and in other embodiments an antibody. Preferred anticancer agents are as described in detail below.

According to another aspect of the invention, a method of enhancing MHC Class II catalyzed peptide exchange is provided. The method involves contacting a cell bearing a MHC Class II molecule with a compound of the formula:

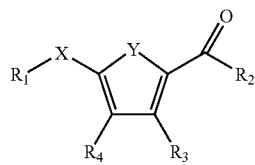

wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and Y is S, in the presence of a peptide that binds MHC class II. The method can be practiced in vitro or in vivo. In one embodiment, the MHC Class II molecule is HLA-DR2. In one embodiment, the MHC class II catalyzed peptide exchange is HLA-DM catalyzed peptide exchange. In one embodiment, the cell is a dendritic cell, a macrophage, a CD 40 activated B cell, or another professional antigen presenting cell. In one embodiment, the peptide is a cancer antigen, a bacterial antigen, a viral antigen, a parasitic antigen or a fungal antigen.

According to another aspect of the invention, a method for treating a subject is provided. The method involves (a) contacting cells bearing a MHC Class II molecule with a compound of the formula:

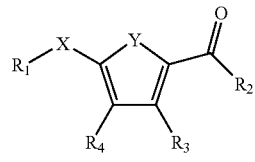

wherein $R_1$ is alkyl, aryl, or heterocyclyl; $R_2$ is H, alkyl, aryl, heterocyclyl, $OR_3$, or $NR_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and Y is S, in the presence of a peptide that binds MHC class II, and (b) administering to a subject in need of such treatment the cells contacted according to (a). In one embodiment, the cells are obtained from the subject and the administration is the re-introduction of the obtained cells to the subject. In one embodiment, the MHC Class II molecule is HLA-DR2. In one embodiment, the MHC class II catalyzed peptide exchange is HLA-DM catalyzed peptide exchange. In one embodiment, the cells are dendritic cells, macrophages, CD 40 activated B cells, or professional antigen presenting cells. In one embodiment, the peptide is a cancer antigen, a bacterial antigen, a viral antigen, a parasitic antigen or a fungal antigen.

According to another aspect of the invention, a method for preparing cells is provided. The method involves administering to a subject a compound of the formula:

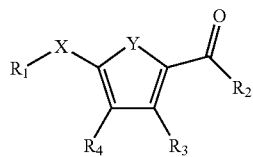

wherein $R_1$ is alkyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and Y is S, and then obtaining immune system cells from the subject. In one embodiment, the immune system cells obtained are T cells. In one embodiment, the immune system cells are dendritic cells, macrophages, CD 40 activated B cells, or professional antigen presenting cells. In one embodiment, the subject has an infectious disease. In one embodiment, the subject has cancer. In one embodiment, the method further involves administering to the subject an antigen that binds MHC Class II.

According to another aspect of the invention, an assay is provided. The assay involves, for example, providing isolated MHC class II molecules with a bound CLIP peptide (class II associated invariant chain peptide), contacting the isolated MHC class II with a test compound, contacting the isolated MHC class II with HLA-DM and with a peptide that binds the isolated MHC class II, measuring the kinetics of binding of the peptide to the isolated WIC class II, and determining whether the test compound enhances binding of the peptide to the isolated MHC class II as compared to a control. In one embodiment, the peptide is fluorescently labeled. In one embodiment, the kinetics of the binding of the peptide to the isolated MHC class II is measured by fluorescence polarization. In one embodiment, the isolated MHC class II is isolated HLA-DR2.

According to another aspect of the invention, a kit is provided. The kit in one embodiment is a package including a first container containing a compound of the formula:

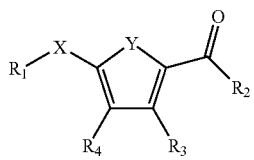

wherein $R_1$ is allyl, aryl, or heterocyclyl; $R_2$ is H, alkyl, aryl, heterocyclyl, $OR_3$, or $N(R_3)_2$; $R_3$ is H, alkyl, aryl, or heterocyclyl; $R_4$ is H, CN, halogen, $CF_3$, $CO_2R_3$, or $C(O)N(R_3)_2$; X is S, $SO_2$, O, or $NR_3$; and Y is S, O, or $NR_3$.

In some embodiments, $R_1$ is alkyl, aryl, or heterocyclyl; $R_2$ is H, aryl, heterocyclyl, $OR_3$, or $N(R_3)_2$; $R_3$ is aryl or heterocyclyl; $R_4$ is H, CN, halogen, $CF_3$, or $C(O)N(R_3)_2$; X is S, $SO_2$, or O; and Y is S or O.

In some embodiments, $R_1$ is alkyl, aryl, or heterocyclyl; $R_2$ is H, $OR_3$, or $N(R_3)_2$; $R_3$ is aryl or heterocyclyl; $R_4$ is H, CN, F, Cl, Br, or $CF_3$; X is S; and Y is S, and a second container containing an antigen. In one embodiment, the antigen is a cancer antigen. In one embodiment, the antigen is a viral antigen, a bacterial antigen, a fungal antigen or a parasitic antigen.

According to another aspect of the invention, a kit is provided. The kit is a package including, for example, a first container containing isolated MHC class II molecules with a bound CLIP peptide, a second container containing a peptide that binds the isolated MHC, and another container containing HLA-DM. In one embodiment, the peptide is fluorescently labeled. In one embodiment, the isolated MHC class II is isolated HLA-DR2.

DETAILED DESCRIPTION

Figure 1:
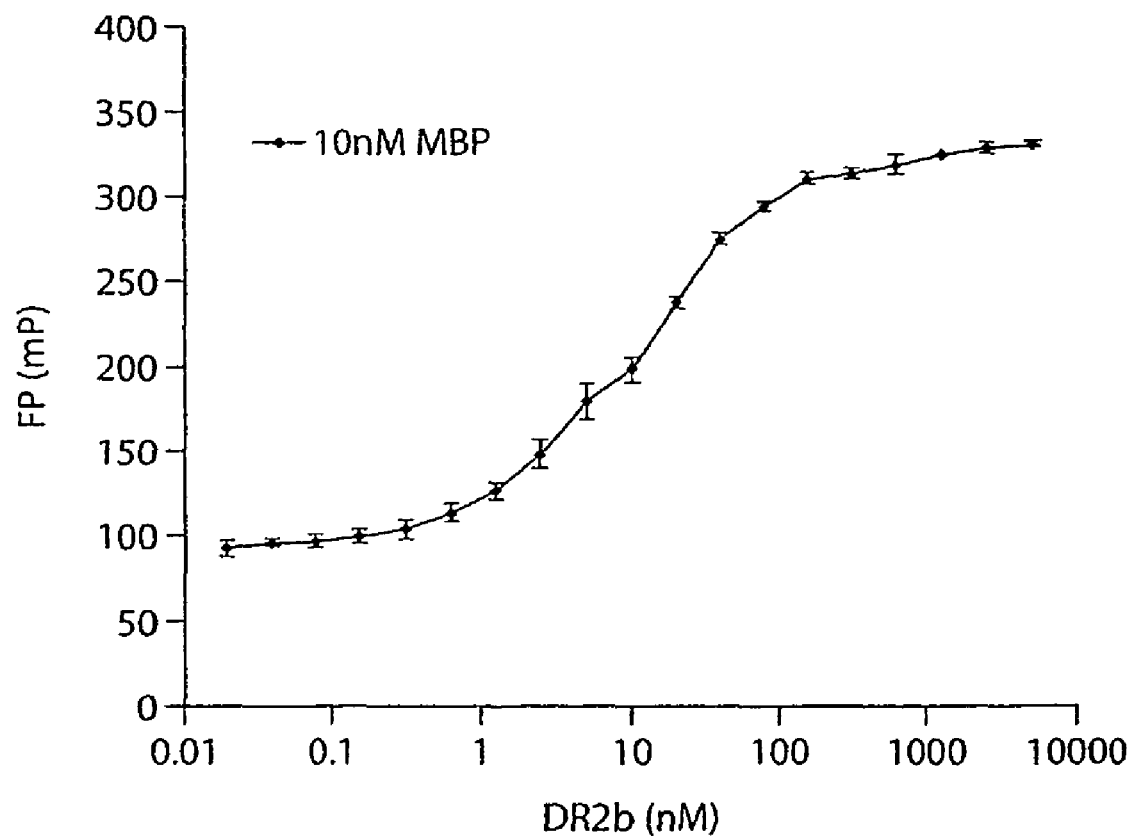
FIG. 1 graphically illustrates an increase in Fluorescence Polarization (indicating binding) at higher concentrations of DR2b in the presence of 10 nM MBP.

In one detailed aspect of the invention, an assay is described below for detecting and monitoring HLA-DM catalyzed peptide exchange. In particular, the kinetics of peptide exchange can be evaluated and the effects on such kinetics of test compounds can be evaluated. A labeled peptide, such as a fluorescently labled MBP peptide, can be visualized binding to isolated HLA-DR2 in the presence of HLA-DM by Fluorescence Polarization (FP). FP can detect the motion of a fluorescently labeled peptide such as MBP (85-99). The FP detected increases when a fluorescently labeled peptide binds to a receptor. This assay may allow peptide binding to HLA-DR2 to be monitored in real time without interrupting the reaction. In this manner, a number of readings can be made at different times during a single assay. This can provide information about the rate of transfer of a peptide, leading to the identification of compounds that increase or decrease the rate of peptide exchange. It may also lead to the identification of compounds that decrease the rate of peptide exchange by directly preventing peptide binding to MHC class II.

The assay described herein may be used, for example, to identify compounds useful in the treatment of a disorder for which a subject would benefit from an increase or decrease in immunological response to a peptide. The present invention involves such an assay, the compounds identified by such an assay, the uses of such compounds as therapeutics and pharmaceutical preparations and kits involving the same. In one embodiment, the invention involves treatment of conditions in which a subject would benefit from an increase in HLA-DM catalyzed peptide exchange. Such conditions include cancer, infectious disease, conditions involving an immunosuppressed state, and autoimmune conditions, where an increase in peptide exchange for higher affinity peptides would benefit a subject.

In one embodiment, the compounds of the invention may be used to modulate an immune response. For example, the compounds of the invention can be used to alter the kinetics of peptide exchange, thereby affecting a subject's repertoire of immune cells specific for an antigen. By influencing peptide exchange, the invention can provide an increase in cells and antibodies with a higher affinity for an antigen. The compounds of the present invention also may be useful in treating a subject with a conditition where an increased CD4 T cell response would benefit the subject. The compounds of the present invention also may be useful in treating a subject with a conditition where an increase in HLA-DM activity would benefit the subject. The compounds of the invention also may be useful for treating viral infections, enhancing tumour immunity, enhancing vaccination efficacy or in ameliorating immune suppression. In one embodiment, the compounds of the invention may be used to up-regulate HLA-DM.

DEFINITIONS

As used herein with respect to polypeptides, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer. Likewise, preferred cycloalkyls have from 3-10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means—$NO_2$; the term "halogen" designates —F, —Cl, —Br or —I; the term "sulfhydryl" means—SH; the term "hydroxyl" means—OH; and the term "sulfonyl" means—$SO_2$—.

The terms "amine" and "amino" are art-recognized and refer to both unsubstituted and substituted amines, e.g., a moiety that can be represented by the general formula:

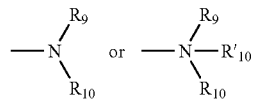

wherein $R_9$, $R_{10}$ and $R'_{10}$ each independently represent a group permitted by the rules of valence.

The term "acylamino" is art-recognized and refers to a moiety that can be represented by the general formula:

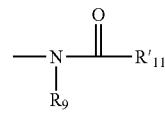

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

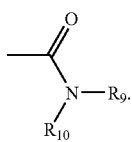

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

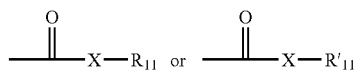

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester". Where X is a sulfur and $R_{11}$ is hydrogen, the formula represents a "thiocarboxylic acid." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

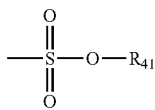

in which $R_{41}$ is an electron pair, hydrogen, alkyl, cycloalkyl, or aryl.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

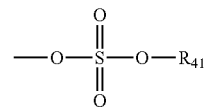

in which $R_{41}$ is as defined above.

The term "sulfonylamino" is art recognized and includes a moiety that can be represented by the general formula:

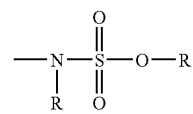

The term "sulfamoyl" is art-recognized and includes a moiety that can be represented by the general formula:

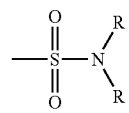

The term "sulfonyl", as used herein, refers to a moiety that can be represented by the general formula:

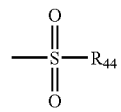

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

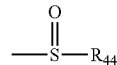

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. Moreover, the enantiomers of a racemic mixture may be separated using chiral chromatography, e.g., chiral HPLC.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

The invention involves in one aspect the treatment of subjects. Subjects as used herein means humans, nonhuman primates, cats, dogs, sheep, goats, horses, cows, pigs and rodents.

The invention involves in one aspect the treatment of subjects having or at risk of having a disease and/or in a state of immunosuppression. For example, the subjects may have or be at risk of developing an infectious disease. In another example, the subject may have or be at risk of developing a cancer. In another example, the subjects may have or may be at risk of developing an immune system suppression, such as from a genetic condition, radiation treatment, chemotherapy, or an infection, such as a chronic infection. Subjects with abnormally low CD 4 cell counts are one example of immune suppressed subjects. In general, the number of functional $CD4^+$-T cells that is within a normal range is known for various mammalian species. In human blood, e.g., the number of functional $CD4^+$-T cells which is considered to be in a normal range is from about 600 to about 1500 $CD4^+$-T cells/$mm^3$ blood. An individual having a number of $CD4^+$-T cells below the normal range, e.g., below about 600/$mm^3$, may be considered "$CD4^+$-deficient"

Subjects may be exposed to myeloid, lymphoid or general immune suppressing conditions by the use of either immunosuppressant drugs such as cyclosporin or high dose chemotherapeutic compounds which affect dividing hemopoietic cells. Immuno-suppression may also arise as a result of treatment modalities such as total body irradiation or conditioning regimens prior to bone marrow transplantation. Viral infection, particularly as in the case of infection with human immunodeficiency virus (HIV), may also immunosuppress an individual. In some embodiments, subjects, are those which have not been exposed and are not anticipated to be exposed to the above-mentioned conditions. In other embodiments, the instant invention aims to treat subjects who may have been myelosuppressed or immunosuppressed (e.g., by exposure to one or more of the above conditions).

The invention thus involves treatment in some embodiments of individuals who are immunocompromised and in other embodiments who are not immunocompromised. Subjects who are not immunocompromised are those that have blood cell counts in the normal range. Subjects who are immunocompromised are those that have blood cell counts below the normal range. Normal ranges of blood counts are known to the medical practitioner and reference can be made to a standard hematology textbook for such counts. In addition, reference can be made to published PCT application PCT/US00/14505.

As mentioned above, the subject may have or be at risk of developing an infectious disease. The agents of the invention thus can used to prevent or treat infectious diseases such as bacterial, viral, fungal, parasitic and myobacterial infections. The agents of The invention can also be used prophylactically to prevent infection during periods of heightened risk, including for example flu season, epidemics, and travel to places where the risk of pathogen exposure is high. The compounds of the invention can prepare a subject for passive exposure to a pathogen.

Examples of bacterial infections include *E. coli*, Streptococcal infections, Staphylococcal infections, *Pseudomonas* infections, *Clostridium difficile*, *Legionella* infections, *Pneumococcus* infection, *Haemophilus* infections (e.g., *Haemophilus influenzae* infections), *Klebsiella* infections, *Enterobacter* infections, *Citrobacter* infections, *Neisseria* infections (e.g., *N. meningitidis* infection, *N. gonorrhoeae* infection), *Shigella* infections, *Salmonella* infections, *Listeria* infections (e.g., *L. monocytogenes* infection), *Pasteurella* infection (e.g., *Pasteurella multocida* infection), *Streptobacillus* infection, *Spirillum* infection, *Treponema* infection (e.g., *Treponema pallidum* infection), *Actinomyces* infection (e.g., *Actinomyces israelli* infection), *Borrelia* infection, *Corynebacterium* infection, *Nocardia* infection, *Gardnerella* infections (e.g., *Gardnerella vaginalis* infection), *Campylobacter* infections (e.g., *Campylobacter fetus* infection), *Spirochaeta* infections, *Proteus* infections, *Bacteriodes* infections, *H. pylori*, and anthrax.

Examples of viral infections include HIV infection, Herpes simplex virus 1 and 2 infections (including encephalitis, neonatal and genital forms), human papilloma virus infection, cytomegalovirus infection, Epstein Barr virus infection, Hepatitis virus A, B and C infections, rotavirus infection, adenovirus infection, influenza A virus infection, respiratory syncytial virus infection, varicella-zoster virus infections, small pox infection, monkey pox infection, and SARS infection. In some embodiments, the methods are not intended to treat or prevent HIV infection.

Examples of fungal infections include candidiasis infection, ringworm, histoplasmosis infection, blastomycosis infections, paracoccidioidomycosis infections, crytococcosis infections, aspergillosis infections, chromomycosis infections, mycetoma infections, pseudallescheriasis infection, and tinea versicolor infection.

Examples of parasite infections include both protozoan infections and nematode infections. These include amebiasis, *Trypanosoma cruzi* infection (i.e., Chagas' disease), Fascioliasis (e.g., *Facioloa hepatica* infection), Leishmaniasis, *Plasmodium* infections (e.g., malaria causing *Plasmodium* species infections, e.g., *P. falciparum, P. knowlesi, P. malariae,*) Onchocerciasis, Paragonimiasis, *Trypanosoma brucei* infection (i.e., Sleeping sickness), *Pneumocystis* infection (e.g., *Pneumocystis carinii* infection), *Trichomonas vaginalis* infection, *Taenia* infections, *Hymenolepsis* infections (e.g., *Hymenolepsis nana* infection), *Echinococcus* infections, Schistosomiasis (e.g., *Schistosoma mansoni* infection), neurocysticercosis, *Necator americanus* infection, and *Trichuris trichuria* infections.

Other infections that can be treated according to the methods of the invention include *Chlamydia* infection, mycobacterial infection such as tuberculosis and leprosy, and Rickettsiae.

The foregoing lists of infections are not intended to be exhaustive but rather exemplary. Those of ordinary skill in the art will identify other infections that are amenable to prevention and treatment using the methods of the invention.

Subjects having an infectious disease are those that exhibit symptoms of infectious disease (e.g., rapid onset, fever, chills, myalgia, photophobia, pharyngitis, acute lymphadenopathy, splenomegaly, gastrointestinal upset, leukocytosis or leukopenia) and in whom infectious pathogens or byproducts thereof can be detected. Tests for diagnosing infectious diseases are known in the art and the ordinary medical practitioner will be familiar with these laboratory tests which include but are not limited to microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject at risk of developing an infectious disease is one that is at risk of exposure to an infectious pathogen. Such subjects include those that live in an area where such pathogens are known to exist and where such infections are common. These subjects also include those that engage in high risk activities such as sharing of needles, engaging in unprotected sexual activity, routine contact with infected samples of subjects (e.g., medical practitioners), people who have undergone surgery, including but not limited to abdominal surgery, etc.

Compounds of the invention are also indicated for treatment of human papillomavirus (HPV) infection. The current therapy for HPV is injection of IFN into a lesion and/or surgical ablation. A systemic treatment such as that envisioned for compounds of the invention would be desirable in comparison with current clinical therapies. Compounds of the invention are similarly useful in combination with HPV vaccines currently in development such as HPV virus-like particle (VLP)-based vaccine (see, for example, Virology 2000 Jan. 20; 266(2):237-45).

The compounds of the invention also may be used to treat a subject who has an infection which is or has become resistant to one or more conventional drug therapies.

The compounds of the invention also are used to treat subjects having or at risk of developing cancer. A subject having a cancer is a subject that has detectable cancerous cells. A subject at risk of developing a cancer is one who has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission.

There are two types of cancers, benign and malignant. Nearly all benign cancers are encapsulated and are noninvasive; in contrast, malignant cancers are almost never encapsulated but invade adjacent tissue by infiltrative destructive growth. This infiltrative growth can be followed by cancer cells implanting at sites discontinuous with the original cancer. The compounds of the invention can be used to treat cancers in humans, including but not limited to: sarcomas, carcinomas, fibromas, leukemias, lymphomas, melanomas, myelomas, neuroblastomas, rhabdomyosarcomas, retinoblastomas, and gliomas, as well as each of the other cancers described herein.

Cancers that migrate from their original location and seed vital organs (thereby giving rise to metastatic lesions) can eventually lead to the death of the subject through the functional deterioration of the affected organs. A metastasis is a region of cancer cells, distinct from the primary cancer location resulting from the dissemination of cancer cells from the primary cancer to other parts of the body. Thus, subjects with metastatic cancers can also be treated according to the invention. In some embodiments, the metastatic cancers are of epithelial origin. Carcinomas may metastasize to bone, as has been observed with breast cancer, and liver, as is sometimes the case with colon cancer. The methods of the invention are intended to treat metastatic cancers regardless of the site of the metastasis and/or the site of the primary cancer.

Cancers include, but are not limited to, basal cell carcinoma, biliary tract cancer; bladder cancer; bone cancer; brain and CNS cancer; breast cancer; cervical cancer; choriocarcinoma; colon and rectum cancer, connective tissue cancer; cancer of the digestive system; endometrial cancer; esophageal cancer; eye cancer; cancer of the head and neck; gastric cancer; germ cell tumors; intra-epithelial neoplasm; Kaposi's sarcoma; kidney cancer; larynx cancer; leukemia (e.g., acute myeloid leukemia, acute lymphoid leukemia, chronic myeloid leukemia and chronic lymphoid leukemia); liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer, renal cell cancer; retinoblastoma; rhabdomyosarcoma; rectal cancer; renal cancer; cancer of the respiratory system; sarcoma; skin cancer; stomach cancer; stromal tumors; testicular cancer; thyroid cancer; uterine cancer; cancer of the urinary system, as well as other carcinomas and sarcomas.

Carcinomas are cancers of epithelial origin that include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hürthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypernephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum. In preferred embodiments, the methods of the invention are used to treat subjects having cancer of the breast, cervix, ovary, prostate, lung, colon and rectum, pancreas, stomach or kidney.

Another particularly important cancer type is sarcomas. Sarcomas are rare mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., non-bone) Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

The invention is used to treat cancers that are immunogenic. Cancers that are immunogenic are cancers that are known to (or likely to) express immunogens on their surface or upon cell death. These immunogens are in vivo endogenous sources of cancer antigens and their release can be exploited by the methods of the invention in order to treat the cancer. The invention also is used to raise antibodies in xenogeneic organisms against cancer antigens. For example, antibodies against human cancer antigens are raised in mice, including mice having substantially human immune systems. Such antibodies can be humanized or already are substatially fully human and can be used in passive immune therapy.

The methods of the invention are also directed towards the treatment of subjects with melanoma. Melanomas are tumors arising from the melanocytic system of the skin and other organs. Examples of melanoma include lentigo maligna melanoma, superficial spreading melanoma, nodular melanoma, and acral lentiginous melanoma.

In some important embodiments of the invention, the methods are particularly directed to subjects at high risk of cancer, such as those predisposed for familial (e.g., familial colon polyposis, BRCA1- or BRCA2-associated breast cancer, Wilms tumour, colorectal cancer, Li-Fraumeni Syndrome, ovarian cancer, and prostate cancer), or non-familial genetic reasons. Subjects at high risk are also those that manifest pre-cancerous symptoms such as pre-cancerous polyps (e.g., in colon cancer), or pre-cancerous lesions (e.g., in HPV-induced cervical cancer).

The cancers to be treated may be refractory cancers. A refractory cancer as used herein is a cancer that is resistant to the ordinary standard of care prescribed. These cancers may appear initially responsive to a treatment (and then recur), or they may be completely non-responsive to the treatment. The ordinary standard of care will vary depending upon the cancer type, and the degree of progression in the subject. It may be a chemotherapy, surgery, or radiation, or a combination thereof. Those of ordinary skill in the art are aware of such standards of care. Subjects being treated according to the invention for a refractory cancer therefore may have already been exposed to another treatment for their cancer. Alternatively, if the cancer is likely to be refractory (e.g., given an analysis of the cancer cells or history of the subject), then the subject may not have already been exposed to another treatment. Examples of refractory cancers include but are not limited to leukemias, melanomas, renal cell carcinomas, colon cancer, liver cancers, pancreatic cancer, and lung cancer.

The compounds of the invention also are used to treat cancers that are known to go into remission. The compounds of the invention also are used to treat cancers that express MHC class II. The compounds of the invention are used to treat, in certain important embodiments, a leukemia, a B-cell lymphoma, a renal carcinoma or a melanoma.

The compounds of the invention also are used to treat subjects who are scheduled to have surgery, radiation treatment, chemotherapy or some other type of immuno-compromising regimen.

The compositions and methods of the invention in certain instances may be useful for replacing existing surgical procedures or drug therapies, although in most instances the present invention is useful in improving the efficacy of existing therapies for treating such conditions. Accordingly combination therapy may be used to treat the subjects that are undergoing or that will undergo a treatment for, inter alia, infectious disease or cancer. For example, the compounds of the present invention can be administered in conjunction with anti-microbial agents or anti-proliferative agents. The compounds of the invention also can be administered in conjunction with other immunotherapies, such as with antigens, adjuvants, immunomodulators, or passive immune therapy with antibodies. The compounds of the invention also can be administered in conjunction with nondrug treatments, such as surgery, radiation therapy or chemotherapy. The other therapy may be administered before, concurrent with, or after treatment with the compounds of the invention. There may also be a delay of several hours, days and in some instances weeks between the administration of the different treatments, such that the compounds of the invention may be administered before or after the other treatment.

In embodiments relating to the treatment of infectious disease, the treatments and compositions provided herein thus can further include anti-microbials agents. Examples of anti-microbials include anti-bacterials, anti-mycobacterials, anti-virals, anti-fungal, and anti-parasites.

Examples of anti-bacterials include β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, and quinolines.

Anti-bacterials include: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphonilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline. Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol;

Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anti-mycobacterials include Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate and Trecator-SC (Ethionamide).

Anti-virals include amantidine and rimantadine, ribivarin, acyclovir, vidarabine, trifluorothymidine, ganciclovir, zidovudine, retinovir, and interferons.

Anti-virals further include: Acemannan; Acyclovir, Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime and integrase inhibitors.

Anti-fungals include imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhibitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); sulfated naphthylamine (e.g., suramin).

Other anti-infectives include Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride; Bithionolate Sodium; Bromchlorenone; Carbamide Peroxide; Cetalkonium Chloride; Cetylpyridinium Chloride; Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene; Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; Troclosene Potassium.

In embodiments relating to the treatment of cancer, the treatments and compositions provided herein thus can further include anti-cancer agents. Examples of anti-cancer drugs can be categorized as DNA damaging agents and these include topoisomerase inhibitors (e.g., etoposide, ramptothecin, topotecan, teniposide, mitoxantrone), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), and radiation therapy.

Suitable anti-cancer compounds to be used in combination with the compounds of the invention include Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-cancer drugs include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; rasGAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Other compounds which are useful in combination therapy for the purpose of the invention include the antiproliferation compound, Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen 1 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

Particularly important anti-cancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-Cl-2' deoxyadenosine; Fludarabine-PO$_4$; mitoxantrone; mitozolomide; Pentostatin; Tomudex.

One particularly important class of anti-cancer agents are taxanes (e.g., paclitaxel and docetaxel). Another important category of anticancer agent is annonaceous acetogenin.

Other cancer therapies include hormonal manipulation, particularly for breast and gynecological cancers. Compounds of the invention thus are also useful in combination with tamoxifen or aromatase inhibitor arimidex (i.e., anastrozole), or simply for disorders responsive to either (e.g., breast cancer). The compounds of the invention can also be combined, and/or administered substantially simultaneously, with enzyme inhibitor agents such as CDK inhibitors, tyrosine kinase inhibitors, MAP kinase inhibitors, and EGFR inhibitors (e.g., C225).

In important embodiments, the agents are administered together with anti-cancer compounds selected from the group consisting of aldesleukin, asparaginase, bleomycin sulfate, carboplatin, chlorambucil, cisplatin, cladribine, cyclophosphamide, cytarabine, dacarbazine, dactinomycin, daunorubicin hydrochloride, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-α2a, interferon-α2b, interferon-αn 3, interferon-α1b, interleukins, irinotecan, mechlorethamine hydrochloride, melphalan, mercatopurine, methotrexate, methotrexate sodium, mitomycin, mitoxantrone, paclitaxel, pegaspargase, pentostatin, prednisone, profimer sodium, procabazine hydrochloride, taxol, taxotere, teniposide, topotecan hydrochloride, vinblastine sulfate, vincristine sulfate and vinorelbine tartrate.

The compounds of the invention also are used with non-drug treatments for cancer, such as with surgical procedures to remove the cancer mass, chemotherapy or radiation therapy. The nondrug therapy may be administered before, concurrent with, or after treatment with the compounds of the invention. There may also be a delay of several hours, days and in some instances weeks between the administration of the different treatments, such that the compounds of the invention may be administered before or after the other treatment.

Surgical methods for treating cancer include intra-abdominal surgeries such as right or left hemicolectomy, sigmoid, subtotal or total colectomy and gastrectomy, radical or partial mastectomy, prostatectomy and hysterectomy.

The invention in one embodiment contemplates the use of compounds of the invention in cancer subjects prior to surgery, radiation or chemotherapy in order to create memory immune cells to the cancer antigen. In this way, memory cells of the immune system can be primed with cancer antigens and thereby provide immune surveillance in the long term. Immune cells so primed can invade a tumor site and effectively clear any remaining tumor debris following the other treatment.

The invention also contemplates the use of compounds of the invention together with other immunotherapies. In one embodiment, the other immunotherapy is treatment with an antigen such as a cancer antigen or a microbial antigen (bacterial antigens, viral antigens, fungal antigens and parasitic antigens). The antigens can be whole antigens, antigen fragments such as peptides, genetically modified antigens, antigens contained in lysates, and the like. The vaccine methods and compositions described herein similarly envision the use of nucleic acid based vaccines in addition to peptide based vaccines. The art is familiar with nucleic acid based vaccines.

Antigens associated with infectious diseases that can be used in the methods of the invention include whole bacteria, whole virus, whole fungi, whole parasites, fragments thereof, lysates thereof, killed versions thereof, etc. The compounds of the invention can be used in combination with various vaccines either currently being used or in development, whether intended for human or non-human subjects. Examples of vaccines for human subjects and directed to infectious diseases include the combined diphtheria and tetanus toxoids vaccine; pertussis whole cell vaccine; the inactivated influenza vaccine; the 23-valent pneumococcal vaccine; the live measles vaccine; the live mumps vaccine; live rubella vaccine; Bacille Calmette-Guerin (BCG) tuberculosis vaccine; hepatitis A vaccine; hepatitis B vaccine; hepatitis C vaccine; rabies vaccine (e.g., human diploid cell vaccine); inactivated polio vaccine; meningococcal polysaccharide vaccine; quadrivalent meningococcal vaccine; yellow fever live virus vaccine; typhoid killed whole cell vaccine; cholera vaccine; Japanese B encephalitis killed virus vaccine; adenovirus vaccine; cytomegalovirus vaccine; rotavirus vaccine; varicella vaccine; anthrax vaccine; small pox vaccine.

The compound of the invention can be used with cancer antigens. A cancer antigen as used herein is a compound differentially associated with a cancer, preferably at the cell surface of a cancer cell (or even at the surface of the neovasculature), that is capable of invoking an immune response. The antigen invokes an immune response when it is presented (in a digested form) on the surface of an antigen presenting cell in the context of an MHC molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A cancer antigen encompasses antigens that are differentially expressed between cancer and normal cells. Due to this differential expression, these antigens can be targeted in anti-tumor therapies. Cancer antigens may be expressed in a regulated manner in normal cells. For example, they may be expressed only at certain stages of differentiation or at certain points in development of the organism or cell. Some are temporally expressed as embryonic and fetal antigens. Still others are never expressed in normal cells, or their expression in such cells is so low as to be undetectable.

Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Examples of cancer antigens include HER 2 (p185), CD20, CD33, GD3 ganglioside, GD2 ganglioside, carcinoembryonic antigen (CEA), CD22, milk mucin core protein, TAG-72, Lewis A antigen, ovarian associated antigens such as OV-TL3 and MOv18, high Mr melanoma antigens recognized by antibody 9.2.27, HMFG-2, SM-3, B72.3, PR5C5, PR4D2, and the like. Other cancer antigens are described in U.S. Pat. No. 5,776,427. Still other cancer antigens are listed in Table 1.

Further examples include MAGE, MART-1/Melan-A, gp100, Dipeptidyl peptidase IV (DPPIV), adenosine deaminase-binding protein (ADAbp), FAP, cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, α-fetoprotein, E-cadherin, α-catenin, β-catenin and γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2.

These antigens can be classified as indicated in Table 1.

TABLE 1

Classification of cancer antigens a. Proteins encoded by genes that have undergone chromosomal alteration in lymphoma and leukemia

| Genes | Disease |
|---|---|
| Activation of quiescent genes | |
| BCL-1 and IgH | Mantel cell lymphoma |
| BCL-2 and IgH | Follicular lymphoma |
| BCL-6 | Diffuse large B-cell lymphoma |
| TAL-1 and TCR☐ or SIL | T-cell acute lymphoblastic leukemia |
| c-MYC and IgH or IgL | Burkitt lymphoma |
| MUN/IRF4 and IgH | Myeloma |
| PAX-5 (BSAP) | Immunocytoma |
| Creation of fusion genes | |
| RARα, PML, PLZF, NPM or NuMA | Acute promyelocytic leukemia |
| BCR and ABL | Chronic myeloid/acute lymphoblastic leukemia |
| MLL (HRX) | Acute leukemia |
| E2A and PBX or HLF | B-cell acute lymphoblastic leukemia |
| NPM, ALK | Anaplastic large cell leukemia |

TABLE 1-continued

| | |
|---|---|
| NPM, MLF-1 | Myelodysplastic syndrome/acute myeloid leukemia |

Adapted from Falini B. and Mason, D.Y. (2002) Blood 99: 409-426 b. Proteins specific to a tissue or cell lineage

| Protein | Disease |
|---|---|
| Cell-surface proteins | |
| CD20, CD22 | Non-Hodgkin's lymphoma, B-cell lymphoma, Chronic lymphocytic leukemia (CLL) |
| CD52 | B-cell CLL |
| CD33 | Acute myelogenous leukemia (AML) |
| CD10 (gp100) | Common (pre-B) acute lymphocytic leukemia and malignant melanoma |
| CD3/T-cell receptor (TCR) | T-cell lymphoma and leukemia |
| CD79/B-cell receptor (BCR) | B-cell lymphoma and leukemia |
| CD26 | Epithelial and lymphoid malignancies |
| Human leukocyte antigen (HLA)-DR, HLA-DP, and HLA-DQ | Lymphoid malignancies |
| RCAS1 | Gynecological carcinomas, bilary adenocarcinomas and ductal adenocarcinomas of the pancreas |
| Prostate specific membrane antigen | Prostate cancer |
| Epidermal growth factor receptors (high expression | |
| EGFR (HER1 or erbB1) and EGFRvIII | Brain, lung, breast, prostate and stomach cancer |
| erbB2 (HER2 or HER2/neu) | Breast cancer and gastric cancer |
| erbB3 (HER3) | Adenocarcinoma |
| erbB4 (HER4) | Breast cancer |
| Cell-associated proteins | |
| Tyrosinase, Melan-A/MART-1, tyrosinase related protein (TRP)-1/gp75 | Malignant melanoma |
| Polymorphic epithelial mucin (PEM) | Breast tumors |
| Human epithelial mucin (MUC1) | Breast, ovarian, colon and lung cancers |
| Secreted proteins | |
| Monoclonal immunoglobulin | Multiple myeloma and plasmacytoma |
| Immunoglobulin light chains | Multiple Myeloma |
| α-fetoprotein | Liver carcinoma |
| Kallikreins 6 and 10 | Ovarian cancer |
| Gastrin-releasing peptide/bombesin | Lung carcinoma |
| Prostate specific antigen | Prostate cancer | c. Cancer testis (CT) antigens*

These antigens include MAGE-A1, -A3, -A6, -A12, BAGE, GAGE, HAGE, LAGE-1, NY-ESO-1, RAGE, SSX-1, -2, -3, -4, -5, -6, -7, -8, -9, HOM-TES-14/SCP-1, HOM-TES-85 and PRAME.

| Protein | Disease |
|---|---|
| SSX-2, and -4 | Neuroblastoma |
| SSX-2 (HOM-MEL-40), MAGE, GAGE, BAGE and PRAME | Malignant melanoma |
| HOM-TES-14/SCP-1 | Meningioma |
| SSX-4 | Oligodendroglioma |
| HOM-TES-14/SCP-1, MAGE-3 and SSX-4 | Astrocytoma |
| SSX member | Head and neck cancer, ovarian cancer, lymphoid tumors, colorectal cancer and breast cancer |
| RAGE-1, -2, -4, GAGE-1, -2, -3, -4, -5, -6, -7 and -8 | Head and neck squamous cell carcinoma (HNSCC) |
| HOM-TES14/SCP-1, SSX-1, PRAME and CT-7 | Non-Hodgkin's lymphoma |
| PRAME | Acute lymphoblastic leukemia (ALL), acute myelogenous leukemia (AML) and chronic lymphocytic leukemia (CLL) |

*These antigens are expressed in some normal tissues such as testis and in some cases placenta. Their expression is common in tumors of diverse lineages and as a group the antigens form targets for immunotherapy. Examples of tumor expression of CT antigens are as follows.

TABLE 1-continued d. Proteins not-specific to a tissue or cell lineage*

Carcinoembryonic antigen (CEA) family: CD66a, CD66b, CD66c, CD66d and CD66e.

*These antigens can be expressed in many different malignant tumors and can be targeted by immunotherapy.

e. Viral proteins

Human papilloma virus protein (cervical cancer)
EBV-encoded nuclear antigen (EBNA)-1 (lymphomas of neck and oral cancer)

f. Mutated or aberrantly expressed molecules

CDK4 and beta-catenin in melanoma

Cancer or tumor antigens can also be classified according to the cancer or tumor they are associated with (i.e., expressed by). Cancers or tumors associated with tumor antigens include acute lymphoblastic leukemia (etv6; aml1; cyclophilin b), B cell lymphoma (Ig-idiotype); Burkitt's (Non-Hodgkin's) lymphoma (CD20); glioma (E-cadherin; α-catenin; β-catenin; γ-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)—C017-1A/GA733; APC), choriocarcinoma (CEA), epithelial cell-cancer (cyclophilin b), gastric cancer (HER2/neu; c-erbB-2; ga733 glycoprotein), hepatocellular cancer (α-fetoprotein), Hodgkin's lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (lmp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), squamous cell cancers of cervix and esophagus (viral products such as human papilloma virus proteins and non-infectious particles), testicular cancer (NY-ESO-1), T cell leukemia (HTLV-1 epitopes), and melanoma (Melan-A/MART-1; cdc27; MAGE-3; p21ras; gp100$^{Pmel17}$).

For examples of tumor antigens which bind to either or both MHC class I and MHC class II molecules, see the following references: Coulie, Stem Cells 13:393-403, 1995; Traversari et al., J. Exp. Med. 176:1453-1457, 1992; Chaux et al., J. Immunol. 163:2928-2936, 1999; Fujie et al., Int. J. Cancer 80:169-172, 1999; Tanzarella et al., Cancer Res. 59:2668-2674, 1999; van der Bruggen et al., Eur. J. Immunol. 24:2134-2140, 1994; Chaux et al., J. Exp. Med. 189:767-778, 1999; Kawashima et al, Hum. Immunol. 59:1-14, 1998; Tahara et al., Clin. Cancer Res. 5:2236-2241, 1999; Gaugler et al., J. Exp. Med. 179:921-930, 1994; van der Bruggen et al., Eur. J. Immunol. 24:3038-3043, 1994; Tanaka et al., Cancer Res. 57:4465-4468, 1997; Oiso et al., Int. J. Cancer 81:387-394, 1999; Herman et al., Immunogenetics 43:377-383, 1996; Manici et al., J. Exp. Med. 189:871-876, 1999; Duffour et al., Eur. J. Immunol. 29:3329-3337, 1999; Zorn et al., Eur. J. Immunol. 29:602-607, 1999; Huang et al., J. Immunol. 162:6849-6854, 1999; Boël et al., Immunity 2:167-175, 1995; Van den Eynde et al., J. Exp. Med. 182:689-698, 1995; De Backer et al., Cancer Res. 59:3157-3165, 1999; Jäger et al., J. Exp. Med. 187:265-270, 1998; Wang et al., J. Immunol. 161:3596-3606, 1998; Aarnoudse et al., Int. J. Cancer 82:442-448, 1999; Guilloux et al., J. Exp. Med. 183:1173-1183, 1996; Lupetti et al., J. Exp. Med. 188:1005-1016, 1998; Wölfel et al., Eur. J. Immunol. 24:759-764, 1994; Skipper et al., J. Exp. Med. 183:527-534, 1996; Kang et al., J. Immunol. 155:1343-1348, 1995; Morel et al., Int. J. Cancer 83:755-759, 1999; Brichard et al., Eur. J. Immunol. 26:224-230, 1996; Kittlesen et al., J. Immunol. 160:2099-2106, 1998; Kawakami et al., J. Immunol. 161:6985-6992, 1998; Topalian et al., J. Exp. Med. 183:1965-1971, 1996; Kobayashi et al., Cancer Research 58:296-301, 1998; Kawakami et al., J. Immunol. 154:3961-3968, 1995; Tsai et al., J. Immunol. 158:1796-1802, 1997; Cox et al., Science 264:716-719, 1994; Kawakami et al., Proc. Natl. Acad. Sci. USA 91:6458-6462, 1994; Skipper et al., J. Immunol. 157:5027-5033, 1996; Robbins et al., J. Immunol. 159:303-308, 1997; Castelli et al, J. Immunol. 162:1739-1748, 1999; Kawakami et al., J. Exp. Med. 180:347-352, 1994; Castelli et al., J. Exp. Med. 181:363-368, 1995; Schneider et al., Int. J. Cancer 75:451-458, 1998; Wang et al., J. Exp. Med. 183:1131-1140, 1996; Wang et al., J. Exp. Med. 184:2207-2216, 1996; Parkhurst et al., Cancer Research 58:4895-4901, 1998; Tsang et al., J. Natl Cancer Inst 87:982-990, 1995; Correale et al., J Natl Cancer Inst 89:293-300, 1997; Coulie et al., Proc. Natl. Acad. Sci. USA 92:7976-7980, 1995; Wölfel et al., Science 269:1281-1284, 1995; Robbins et al., J. Exp. Med. 183:1185-1192, 1996; Brändle et al., J. Exp. Med. 183:2501-2508, 1996; ten Bosch et al., Blood 88:3522-3527, 1996; Mandruzzato et al., J. Exp. Med. 186:785-793, 1997; Guéguen et al., J. Immunol. 160:6188-6194, 1998; Gjertsen et al., Int. J. Cancer 72:784-790, 1997; Gaudin et al., J. Immunol. 162:1730-1738, 1999; Chiari et al., Cancer Res. 59:5785-5792, 1999; Hogan et al., Cancer Res. 58:5144-5150, 1998; Pieper et al., J. Exp. Med. 189:757-765, 1999; Wang et al., Science 284:1351-1354, 1999; Fisk et al., J. Exp. Med. 181:2109-2117, 1995; Brossart et al., Cancer Res. 58:732-736, 1998; Röpke et al., Proc. Natl. Acad. Sci. USA 93:14704-14707, 1996; Ikeda et al., Immunity 6:199-208, 1997; Ronsin et al., J. Immunol. 163:483-490, 1999; Vonderheide et al., Immunity 10:673-679, 1999. These antigens as well as others are disclosed in PCT Application PCT/US98/18601.

In some preferred embodiments, the cancer antigen is VEGF, Anti-idiotypic mAb (GD3 ganglioside mimic), CD20, CD52, Anti-idiotypic mAb (CEA mimic), ERBB2, EGFR, CD22, ERBB2 X CD65 (fcγRI), EpCam, PEM and CD33.

The invention also seeks to enhance other forms of immunotherapy including dendritic cell vaccines. These vaccines generally include dendritic cells loaded ex vivo with antigens such as tumor-associated antigens. The dendritic cells can be incubated with the antigen, thereby allowing for antigen processing and expression on the cell surface, or the cells may simply be combined with the antigen prior to injection in vivo. Alternatively, the dendritic cells may be activated in vitro and then re-infused into a subject in the activated state. Compounds of the invention can be combined with the dendritic cells in all of these embodiments. Examples of dendritic cell based vaccines include autologous tumour antigen-pulsed dendritic cells (advanced gynaecological malignancies); blood-derived dendritic cells loaded ex vivo with prostate cancer antigen (Provenge; Dendreon Corporation); blood-derived dendritic cells loaded ex vivo with antigen for multiple myeloma and other B-cell malignancies (Mylovenge; Dendreon Corporation); and blood-derived dendritic cells loaded ex vivo with antigen for cancers expressing the HER-2/neu proto-oncogene (APC8024; Dendreon Corporation); xenoantigen (e.g., PAP) loaded dendritic cells, and the like.

The compounds of the invention also may be used in conjuction with pasive immune therapy. The antibodies that can be used with the compounds of the invention include those useful in cancer and infectious disease as well as other disorders for which antibodies and antigens have been identified and which would benefit from an enhanced immune response.

The antibodies or fragments thereof useful in the invention can be specific for any component of a particular target. Accordingly, the antibody can recognize and bind to proteins, lipids, carbohydrates, DNA, RNA, and any combination of these in molecular or supra-molecular structures (e.g., cell organelles such as mitochondria or ribosomes). The antibody or fragment thereof can also recognize a modification of the tumor cell, such as e.g., chemical modifications, or genetic modifications made by transfection ex vivo or in vivo with DNA or RNA. As used herein, the terms "antibody" and "immunoglobulin" are used interchangeably.

Bispecific antibodies can also be used in the invention. A bispecific antibody is one having one variable region that specifically recognizes a tumor antigen and the other variable region that specifically recognizes an antigenic epitope of a host immune effector cell that has lytic or growth inhibitory activity against the tumor. Bispecific and multispecific antibody complexes can be created by linkage of two or more immunoglobulins of different specificity for tumor antigens and/or effector cell antigens, either at the peptide or nucleic acid level.

Immunoglobulin can be produced in vivo in human or non-human species, or in vitro from immunoglobulin encoding DNA or cDNA isolated from libraries of DNA (e.g., phage display libraries). Immunoglobulin can also be modified genetically or chemically to incorporate human polypeptide sequences into non-human coding sequences (commonly referred to as humanization). Additionally, immunoglobulins can be modified chemically or genetically to incorporate protein, lipid, or carbohydrate moieties. Potential modifications could also include naturally occurring or synthetic molecular entities that are either directly toxic for tumor cells or serve as ligands or receptors for biologically active molecules that could suppress tumor growth. For example, growth factors, cytokines, chemokines and their respective receptors, immunologically active ligands or receptors, hormones or naturally occurring or synthetic toxins all represent biologically active molecules that could interact with suitably modified immunoglobulins and their targets.

As used herein, an "anti-cancer antibody or fragment thereof" is an antibody or an antibody fragment that binds to a cancer or tumor antigen. Some commercially available anti-cancer antibodies along with their commercial source are as follows: anti-CD20 mAb (monoclonal antibody), rituximab, (Rituxan™, IDEC-Y2Bf), Rituxan™, Non-Hodgkin's lymphoma, B cell lymphoma (IDEC/Genentech); anti-CD20 mAb, tositumomab Bexxar, Non-Hodgkin's lymphoma (Corixa/GlaxoSmithKline); anti-HER2, trastuzumab, Herceptin™, breast and ovarian cancer (Genentech); anti-HER2, MDX-210, prostate, non-small cell lung cancer, breast, pancreatic, ovarian, renal and colon cancer (Medarex/Novartis); anti-CA125 mAb, oregovomab, B43.13, Ovarex™, ovarian cancer (Altarex); Breva-Rex, multiple myeloma, breast, lung, ovarian (Altarex); AR54, ovarian, breast, lung (Altarex); GivaRex, pancreas, stomach, colorectal (Altarex); ProstaRex, prostate (Altarex); anti-EGF receptor mAb, IMC-C225, Erbitux™, breast, head and neck, non-small cell lung, renal, prostate, colorectal and pancreatic cancer (ImClone Systems); anti-EGF receptor mAb, MDX-447, head and neck, prostate, lung, bladder, cervical, ovarian cancer (Medarex/Merck); gemtuzumab ozogamicin, Mylotarg, CMA-676, anti-CD33 (Wyeth Pharmaceuticals); anti-tissue factor protein (TF), (Sunol); ior-c5, colorectal cancer; ceal, colorectal cancer; c5, colorectal cancer; anti-EGF receptor mAb, MDX-447, head and neck, prostate, lung, bladder, cervical and ovarian cancer (Medarex/Merck); anti-17-1A mAb, edrecolomab, Panorex, colorectal, pancreatic, lung, breast and ovarian cancer (Centocor/Glaxo/Ajinomoto); anti-CD20 mAb (Y-90 labeled), ibritumomab tiuxetan (IDEC-Y2B8), Zevalin, Non-Hodgkin's lymphoma (IDEC); anti-idiotypic mAb mimic of ganglioside GD3 epitope, BEC2, small cell lung carcinoma, melanoma (ImClone Systems); anti-HLA-Dr10 mAb (131 I LYM-1), Oncolym™, Non-Hodgkin's lymphoma (Peregrine Pharmaceuticals); anti-CD33 humanized mAb (SMART M195), Zamyl™, acute myeloid leukemia, acute promyelocytic leukemia (Protein Design Labs); anti-CD52 humAb (LDP-03), CAMPATH, chronic lymphocytic leukemia (Millenium Pharmaceuticals/Ilex Oncology); anti-CD1 mAb, ior t6, cancer (Center of Molecular Immunology); anti-CAR (complement activating receptor) mAb, MDX-11, myeloid leukemia (Medarex); humanized bispecific mAb conjugates (complement cascade activators), MDX-22, myeloid leukemia (Medarex); OV103 (Y-90 labeled antibody), celogovab, OncoScint™, ovarian and prostate cancer (Cytogen); anti-17-1A mAb, 3622W94, non-small cell lung carcinoma, prostate cancer (Glaxo Wellcome plc); anti-VEGF (RhumAb-VEGF), bevacizumab, Avastin™, lung, breast, prostate, renal and colorectal cancer (Genentech); anti-TAC (IL-2 receptor) humanized Ab (SMART), daclizumab, Zenapax, leukemia, lymphoma (Protein Design Labs); anti-TAG-72 partially humanized bispecific Ab, MDX-220, lung, colon, prostate, ovarian, endometrial, pancreatic and gastric cancer (Medarex); anti-idiotypic mAb mimic of high molecular weight proteoglycan (I-Mel-1), MELIMMUNE-1, melanoma (IDEC); anti-idiotypic mAb mimic of high molecular weight proteoglycan (I-Mel-2), MELIMMUNE-2, melanoma (IDEC); anti-CEA Ab (hMN14), CEACide™, colorectal cancer and other cancers (Immunomedics); Pretarget™ radioactive targeting agents, cancer (NeoRx); hmAbH11 scFv fragment (NovomAb-G2), H11 scFv, cancer (Viventia Biotech); anti-DNA or DNA-associated proteins (histones) mAb and conjugates, TNT (e.g. Cotara™), cancer (Peregrine Pharmaceuticals); Gliomab-H mAb, brain cancer, melanoma, neuroblastoma (Viventia Biotech); GNI-250 mAb, colorectal cancer (Wyeth); anti-EGF receptor mAb, EMD-72000, cancer (Merck KgaA); anti-CD22 humanized Ab, LymphoCide, Non-Hodgkin's lymphoma (Immunomedics); anti-CD33 mAb conjugate with calicheamicin (CMA 676), gemtuzumab ozogamicin, Mylotarg™, acute myelogenous leukemia (Wyeth); Monopharm-C, colon, lung and pancreatic cancer (Viventia Biotech); anti-idiotypic human mAb to GD2 ganglioside, 4B5, melanoma, small-cell lung cancer, neuroblastoma (Viventia Biotech); anti-EGF receptor humanized Ab, ior egf/r3, cancers of epithelial origin (Center of Molecular Immunology); anti-ior c2 glycoprotein mAb, ior c5, colorectal and ovarian cancer (Center of Molecular Immunology); BABS (biosynthetic antibody binding site) proteins, breast cancer (Chiron); anti-FLK-2/FLT-3 mAb, cancer (tumor-associated angiogenesis) (ImClone Systems); mAb/small-molecule conjugate, TAP (tumor-activated prodrug), cancer (ImmunoGen); anti-GD-2 bispecific mAb, MDX-260, melanoma, glioma, neuroblastoma (Medarex); antinuclear autoantibodies (binds nucleosomes), ANA Ab, cancer (Procyon Biopharma); anti-HLA-DR Ab (SMART 1D10 Ab), Remitogen™, Non-Hodgkin's B-cell lymphoma (Protein Design Labs); SMART ABL 364 Ab, epithelial cell cancers, breast, lung and colon cancer (Protein Design Labs/Novartis); anti-CEA I131-labeled mAb, ImmuRAIT-CEA, colorectal cancer (Immunomedics).

The antibody or antibody fragment provided herein can be used additionally for delivery of toxic substances to cancer cells. They may be conjugated (covalently or otherwise) to a toxin derived from plant, fungus, or bacteria. The toxin may be selected from the group consisting of A chain toxin, deglycosylated A chain toxin, ribosome inactivating protein, α-sarcin, aspergillin, restrictocin, ribonuclease, diptheria toxin, *Pseudomonas* exotoxin, to calicheamicin, maytansinoids and ricin (e.g., from castor beans), but is not so limited. The antibody or antibody fragment may also conjugated to a chemotherapeutic agent, biological response modifiers, radioisotopes such as Iodine-131 and Yttrium-90 or those recited herein, or a cytotoxin. The chemotherapeutic agent may be selected from the group consisting of an anti-metabolite, an anthracycline, a vinca alkaloid, an antibiotic, an alkylating agent, and an epipodophyllotoxin, but is not so limited. The toxic substances can be concentrated in the desired region (e.g., a tumor) and non-specific toxicity to normal cells can be minimized. Antibodies to cancer antigens, vasculature, and microbial antigens can be modified in this manner. Antibodies to vasculature are particularly important because, generally, solid tumors are dependent upon newly formed blood vessels to survive. As a result, one strategy of many cancer medicaments is to attack the blood vessels feeding a tumor and/or the connective tissues (or stroma) supporting such blood vessels.

The invention also embraces treatment using antibodies and fragments thereof directed to stromal cell molecules and tumor vasculature associated molecules. A stromal cell molecule is a molecule expressed by a stromal cell. Examples include but are not limited to FAP and CD26. A tumor vasculature associated molecule is a molecule expressed by vasculature of a tumor (i.e., a solid cancer rather than a systemic cancer such as leukemia). As with a cancer antigen, a tumor vasculature associated molecule may be expressed by normal vasculature, however its presence on vasculature of a tumor makes it a suitable target for anti-cancer therapy. In some instances, the tumor vasculature associated molecule is expressed at a higher level in tumor vasculature than it is in normal vasculature. Examples include but are not limited to endoglin (see U.S. Pat. No. 5,660,827), ELAM-1, VCAM-1, ICAM-1, ligand reactive with LAM-1, MHC class II antigens, aminophospholipids such as phosphatidylserine and phosphatidylethanolamine (as described in U.S. Pat. No. 6,312,694), VEGFR1 (Flt-1) and VEGFR2 (KDR/Flk-1), and other tumor vasculature associated antigens such as those described in U.S. Pat. No. 5,776,427. Antibodies to endoglin are described in U.S. Pat. No. 5,660,827 and include TEC-4 and TEC-11, and antibodies that recognize identical epitopes to these antibodies. Antibodies to aminophospholipids are described in U.S. Pat. No. 6,312,694. Antibodies that inhibit VEGF are described in U.S. Pat. No. 6,342,219 and include 2C3 (ATCC PTA 1595). Other antibodies that are specific for tumor vasculature include antibodies that react to a complex of a growth factor and its receptor such as a complex of FGF and the FGFR or a complex of TGFβ and the TGFβR. Antibodies of this latter class are described in U.S. Pat. No. 5,965, 132, and include GV39 and GV97.

In some preferred embodiments of the invention, the antibodies are Avastin (bevacizumab), BEC2 (mitumomab), Bexxar (tositumomab), Campath (alemtuzumab), CeaVac, Herceptin (trastuzumab), IMC-C225 (centuximab), Lympho-Cide (epratuzumab), MDX-210, Mylotarg (gemtuzumab ozogamicin), Panorex (edrecolomab), Rituxan (rituximab), Theragyn (pemtumomab), Zamyl, and Zevalin (ibritumomab tituxetan). The invention also covers antibody fragments thereof.

Other antibodies that can be used according to the invention include anti-TNFα antibody such as infliximab (Remicade) and etanercept (Enbrel) for rheumatoid arthritis and Crohn's disease palivizumab; anti-RSV antibody for pediatric subjects; bevacizumab, breast cancer; alemtuzumab, Campath-1H, breast and renal cancer, melanoma, B cell chronic lymphocytic leukemia (Millennium and ILEX); BLyS-mAb, fSLE and rheumatoid arthritis; anti-VEGF2, melanoma, breast cancer; anti-Trail receptor; B3 mAb, breast cancer; m170 mAb, breast cancer; mAB BR96, breast cancer; Abx-Cbl mAb, graft versus host disease.

The invention also embraces the use of immunomodulatory agants in combination with the compounds and treatments of the invention. One type of such agents is adjuvants, which heighten the immune response. Adjuvants that may be combined with the compounds of Formula I include nucleic acid adjuvants and on-nucleic acid adjuvants.

A "nucleic acid adjuvant" is an adjuvant that is a nucleic acid or analog thereof. Examples include immunostimulatory nucleic acid molecules such as those containing CpG dinucleotides, as described in U.S. Pat. No. 6,194,388B1, issued Feb. 27, 2001, U.S. Pat. No. 6,207,646 B1, issued Mar. 27, 2001, and U.S. Pat. No. 6,239,116 B1, issued May 29, 2001.

A "non-nucleic acid adjuvant" is any molecule or compound other than immunostimulatory nucleic acids, which can stimulate the humoral and/or cellular immune response. Non-nucleic acid adjuvants include, for instance, adjuvants that create a depo effect, immune-stimulating adjuvants, adjuvants that create a depo effect and stimulate the immune system and mucosal adjuvants.

An "adjuvant that creates a depo effect" as used herein is an adjuvant that causes an antigen, such as a cancer antigen present in a cancer vaccine, to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC Pharmaceuticals Corporation, San Diego, Calif.).

An "immune stimulating adjuvant" is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the 21$^{st}$ peak with HPLC fractionation; Antigenics, Inc., Waltham, Mass.); poly [di (carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

"Adjuvants that create a depo effect and stimulate the immune system" are those compounds which have both of the above-identified functions. This class of adjuvants includes but is not limited to ISCOMS (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); nonionic block copolymers that form micelles such as CRL 1005 (these contain a linear chain of hydrophobic polyoxpropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A "non-nucleic acid mucosal adjuvant" as used herein is an adjuvant other than an immunostimulatory nucleic acid that is capable of inducing a mucosal immune response in a subject when administered to a mucosal surface in conjunction with an antigen. Mucosal adjuvants include but are not limited to Bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN$_{107}$ (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protine of *Neisseria meningitidis*)(Marinaro et al., 1999, Van de Verg et al., 1996); Oil-in-water emulsions (e.g., MF59) (Barchfield et al., 1999, Verschoor et al., 1999, O'Hagan, 1998); Aluminum salts Osaka et al., 1998, 1999); and Saponins (e.g., QS21) Aquila Biopharmaceuticals, Inc., Worcester, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and *Leishmania* elongation factor (Corixa Corporation, Seattle, Wash.).

The compounds of the invention can also be combined with other immunomodulatory agents for enhancing an immune response to an antigen, such as cytokines, chemokines, and growth factors with stimulate heatopoietic cells. Immune responses can be induced or augmented by cytokines or chemokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) The cytokines and/or chemokines can be administered directly or may be administered in the form of a nucleic acid vector that encodes the cytokine, such that the cytokine can be expressed in vivo. In one embodiment, the cytokine or chemokine is administered in the form of a plasmid expression vector. The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Cytokines also are central in directing the T cell response.

Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (IFN-γ), IFN-α, tumor necrosis factor (TNF), TGF-β, FLT-3 ligand, and CD40 ligand. In some embodiments, the cytokine is a Th1 cytokine. In still other embodiments, the cytokine is a Th2 cytokine.

The term "chemokine" is used as a generic name for peptides or polypeptides that act principally to chemoattract effector cells of both innate and adaptive immunity. Chemokines are thought to coordinate immunological defenses against tumors and infectious agents by concentrating neutrophils, macrophages, eosinophils and T and B lymphocytes at the anatomical site in which the tumor or infectious agent is present. In addition, many chemokines are known to activate the effector cells so that their immune functions (e.g., cytolysis of tumor cells) are enhanced on a per cell basis. Two groups of chemokines are distinguished according to the positions of the first two cysteine residues that are conserved in the amino-terminal portions of the polypeptides. The residues can either be adjacent or separated by one amino acid, thereby defining the CC and CXC cytokines respectively. The activity of each chemokine is restricted to particular effector cells, and this specificity results from a cognate interaction between the chemokine and a specific cell membrane receptor expressed by the effector cells. For example, the CXC chemokines IL-8, Groα/β and ENA 78 act specifically on neutrophils, whereas the CC chemokines RANTES, MIP-1α and MCP-3 act on monocytes and activated T cells. In addition, the CXC chemokine IP-10 appears to have anti-angiogenic activity against tumors as well as being a chemoattractant for activated T cells. MIP-1α also reportedly has effects on hemopoietic precursor.

Growth factors useful according to the invention include erythropoietin (U.S. Pat. No. 4,703,008) and analogs thereof, dipeptidylpeptidase inhibitors, Platelet Derived Growth Factor (PDGF) (U.S. Pat. No. 4,766,073), Platelet Derived Endothelial Cell Growth Factor (PD-ECGF) (U.S. Pat. No. 5,227,302), Human pituitary Growth Hormone (HGH) (U.S. Pat. No. 3,853,833), Transforming Growth Factor Beta (TGF.beta.) (U.S. Pat. No. 5,168,051), Transforming Growth Factor Alpha (TGF.alpha.) (U.S. Pat. No. 5,633,147), Keratinocyte Growth Factor (KGF) (U.S. Pat. No. 5,731,170), Insulin-like Growth Factor I (IGF-I) (U.S. Pat. No. 4,963,665), Epidermal Growth Factor (EGF) (U.S. Pat. No. 5,096,825), Erythropoietin (EPO), Granulocyte-Macrophage Colony Stimulating Factor (GM-CSF) (U.S. Pat. No. 5,200,327), M-CSF (U.S. Pat. No. 5,171,675), Colony Stimulating Factor-1 (CSF-1) (U.S. Pat. No. 4,847,201), Steel factor, Calcitonin, AP-1 proteins (U.S. Pat. No. 5,238,839), Brain Derived Neurotrophic Factor (BDNF) (U.S. Pat. No. 5,229,500). All of the references cited above are incorporated herein by reference in their entirety.

The pharmaceutical formulations of the invention contain a compound of the invention in a pharmaceutically acceptable carrier suitable for administration and delivery in vivo. The pharmaceutical compositions of the present invention are formulated for oral, sublingual, buccal, intranasal, inhalation, injection (subcutaneous, intraveneous, intrathecal, intraperitoneal, etc.) or infusion. When administered, the compounds of the invention are administered in pharmaceutically acceptable preparations. Such preparations may routinely contain pharmaceutically acceptable concentrations of salt, buffering agents, preservatives, compatible carriers, and the like. The pharmaceutical preparations of the invention also can contain immunomodulaotry agents, anti-cancer agents, anti-microbials, and/or antigens. Thus, "cocktails" are contemplated.

The preferred amount of the compounds of the invention is a therapeutically effective amount thereof which is also medically acceptable. Actual dosage levels of in the pharmaceutical compositions of the present invention may be varied so as to obtain an amount which is effective to achieve the desired therapeutic response for a particular patient, pharmaceutical composition, and mode of administration, without being toxic to the patient. The selected dosage level and frequency of administration will depend upon a variety of factors including the route of administration, the time of administration, the duration of the treatment, other drugs, compounds and/or materials used in combination with the compounds of the invention, the age, sex, weight, condition, general health and prior medical history of the patient being treated, and the like factors well known in the medical arts. A physician having ordinary skill in the art can readily determine and prescribe the therapeutically effective amount of the pharmaceutical composition required.

Effective amounts can be determined, for example, by measuring increases in the immune response, for example, by the presence of higher titers of antibody, the presence of higher affinity antibodies, the presence of a desired population of immune cells such as memory cells to a particular antigen, or the presence of particular antigen specific cytotoxic T cells. Effective amounts also can be measured by a reduction in microbial load in the case of an infection or in the size or progression of a tumor in the case of cancer. An effective amount also may be reflected in a reduction in the symptoms experienced by a particular subject being treated.

Dosage may be adjusted appropriately to achieve desired drug levels, locally or systemically. Generally, daily doses of compounds will be from about 0.001 mg/kg per day to 1000 mg/kg per day. It is expected that doses in the range of about 0.1 to 50 mg/kg per day will be effective. In the event that the response in a subject is insufficient at such doses, even higher doses (or effective higher doses by a different, more localized delivery route) may be employed to the extent that patient tolerance permits.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Oral and intravenous routes are preferred.

For transmucosal delivery, delivery is typically in the form of a solid as a lingual, buccal or sublingual tablet, troche (lozenge), powder, time-release granules, pellets or the like, or in the form of a liquid as a liquid drop or drops, aerosol spray or mist.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For administration by injection, conventional carriers well known to those of ordinary skill in the art can be used.

Other delivery systems can include time-release, delayed release or sustained release delivery systems. Such systems can avoid repeated administrations of the conjugates of the invention, increasing convenience to the subject and the physician. Many types of release delivery systems are available and known to those of ordinary skill in the art. They include polymer based systems such as polytactic and polyglycolic acid, polyanhidrides and to polycaprolactone; wax coatings, compressed tablets using conventional binders and excipients, and the like. Bioadhesive polymer systems to enhance delivery of a material to the intestinal epithelium are known and described in published PCT application WO 93/21906. Capsules for delivering agents to the intestinal epithelium also are described in published PCT application WO 93/19660.

Compositions may be conveniently presented in unit dosage form and may be prepared by any of the methods well known in the art of pharmacy. All methods include the step of bringing the conjugate into association with a carrier which constitutes one or more accessory, ingredients. In general, the compositions are prepared by uniformly and intimately bringing the conjugate into association with a liquid carrier, a finely divided solid carrier, or both, and then, if necessary, shaping the product.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. In some embodiments, the pack or dispenser device is a kit which includes at least a compound of the present invention together with instructions for use. The kit may optionally include any one of or any combination of: (i) one or more diluants, (ii) an antigen, (iii) an anti-microbial agent or and anti-cancer agent, and (iv) an immune mudulatory agent such as an adjuvant, a cytokine, a chemokine, or a growth factor.

A kit may include, for example, a container containing a first vial that houses a compound of the invention. A second vial may contain an antigen and an adjuvant. A syringe may be provided for mixing the contents of the first and second vial. Instructions for operation may also be provided.

Buffers in general are well known to those of ordinary skill in the art. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

Chelating agents are chemicals which form water soluble coordination compounds with metal ions in order to trap or remove the metal irons from solution, thereby avoiding the degradative effects of the metal ions. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid, also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof. Another well known chelating agent is L-glutamic acid, N,N-diacetic acid and derivatives thereof (also known as GLDA). Derivatives include monosodium L-glutamic acid N,N-diacetic acid.

The pharmaceutical preparations of the invention also may include isotonicity agents. This term is used in the art interchangeably with iso-osmotic agent, and is known as a compound which is added to the pharmaceutical preparation to increase the osmotic pressure to that of 0.9% sodium chloride solution, which is iso-osmotic with human extracellular fluids, such as plasma. Preferred isotonicity agents are sodium chloride, mannitol, sorbitol, lactose, dextrose and glycerol.

Optionally, the pharmaceutical preparations of the invention may further comprise a preservative. Suitable preservatives include but are not limited to: chlorobutanol (0.3-0.9% W/V), parabens (0.01-5.0%), thimerosal (0.004-0.2%), benzyl alcohol (0.5-5%), phenol (0.1-1.0%), and the like.

Compound F15 is available from Maybridge (Cornwall, UK) as catalog number KM 02773. Alternatively, F15 may be synthesized by methods known to those skilled in the art, such as those described below.

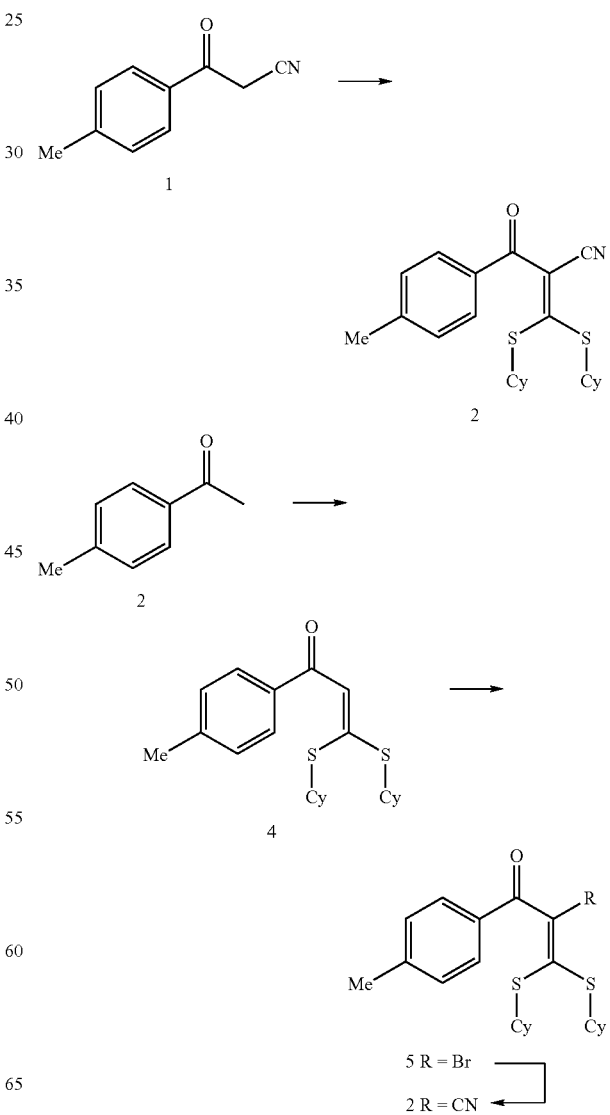

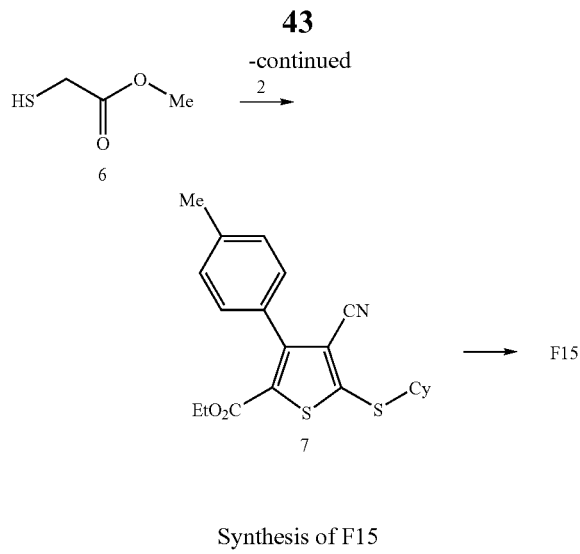

Synthesis of F15

Compound 1 can be converted to 2 utilizing the method of Doelling, et al. (*Phosphorus, Sulfur, Silicon, Relat. Elem* 1994, 86, 129). Alternatively, 3 can be converted to 4 using the procedure of Curphey, et al. (*Tetrahedron Lett.* 2000, 41, 6977). This compound can be brominated with N-bromosuccinimide to give 5 using the method of Yamamoto (*Bull. Chem. Soc., Jpn.* 1992, 65, 1550). The bromide 5 is converted to 2 using copper cyanide following the described procedure of Singh (*Synthesis* 1985, 2, 165). Compound 2 can be converted to thiophene 7 by allowing it to react with 6 according to the method of Abdulla, et al. (EP 273602, 1988). Finally, saponification of the ester gives F15.

HLA-DR2 is the MHC class II allele that has been implicated in susceptibility to multiple sclerosis. It is believed that HLA-DM catalyzes the exchange of peptides that bind to MHC Class II molecules such as HLA-DR, HLA-DQ and HLA-DP. There are many known alleles (142) in various species. It is believed that acceleration of the presentation of peptides to HLA-DR2 may accelerate a step in the presentation of antigens to CD4 T cells. HLA-DR2 may present CLIP that may be exchanged for another peptide that binds HLA-DR2, such as a peptide from an exongenous antigen. This exchange is believed to be catalyzed by HLA-DM.

In the assay described below (Antigen Presentation Screen), Fluorescence Polarization (FP) can be used to monitor the kinetics, including the exchange rate, of exchanging CLIP for myelin basic protein (MBP) peptide on isolated HLA-DR2. MBP peptide consisting of amino acids 85-99 of Myelin Basic Protein is labeled with the fluorescent dye Alexa 488 at the P5 position. The CLIP may be unlabled. A system of isolated HLA-DR2 containing CLIP and labeled MBP peptide are incubated in the presence of HLA-DM. The system may be exposed to test compounds and FP can be used to measure the rate of exchange of CLIP for MBP for each test compound, including a control. A change in fluorescence polarization is monitored and/or recorded using a 485 nm excitation filter and a 530 nm emission filter in a LJL Analyst. Fluorescence readings taken at time intervals can indicate how fast CLIP is being exchanged for MBP in the presence of HLA-DM.

Antigen Presentation Screen

Materials

Buffer: 50 mM Citrate pH 5.2 (pH with HCl)/150 mM NaCl (Sodium Citrate: Fisher Scientific S279-500, Sodium Chloride: Fisher Scientific S271-3)

Proteins: HLA-DR2b containing the CLIP peptide in PBS buffer synthesized by COS cells with covalently linked CLIP peptide. The linker is cut with the addition of 25 U/ml of Thrombin (Novagen 69671) (2 hr incubation at 37° C.) and blocked with Pefablock (Roche 1429-868).

HLA-DM in PBS buffer, synthesized in S2 insect cells. Purified on a anti-FLAG column with a high pH elution (50 mM CAPS pH 11.5)

Peptides: MBP 85-99 (Alexa 488 at P5 position) in $H_2O$
   H2N-ENPVVHFF(C-Alexa 488 ($C_5$ maleimide) (Molecular Probes))NIVTPR-OH (New England Peptide, Inc)
   MBP 85-99 (unlabeled) in $H_2O$
   H2N-ENPVVHFFKNIVTPR-OH (New England Peptide, Inc)

384 well Plate: Corning Costar 384 well polystyrene plate (Fisher Scientific #07-201-104 Corning #3654).

FIGS. 6-12 illustrate (shaded wells) to which wells particular reagents or compounds were added, as described below.

Final Reaction Conditions 100 nM HLA-DR2b
100 nM HLA-DM **
10 nM MBP (Alexa 488 at P5)
1% DMSO
50 µM Library Compound (adjustable)

**This is approximate as some batches are more active than others—amount used is based on what concentration is required to complete the reaction in 6 hours.

Controls

Figure 6:
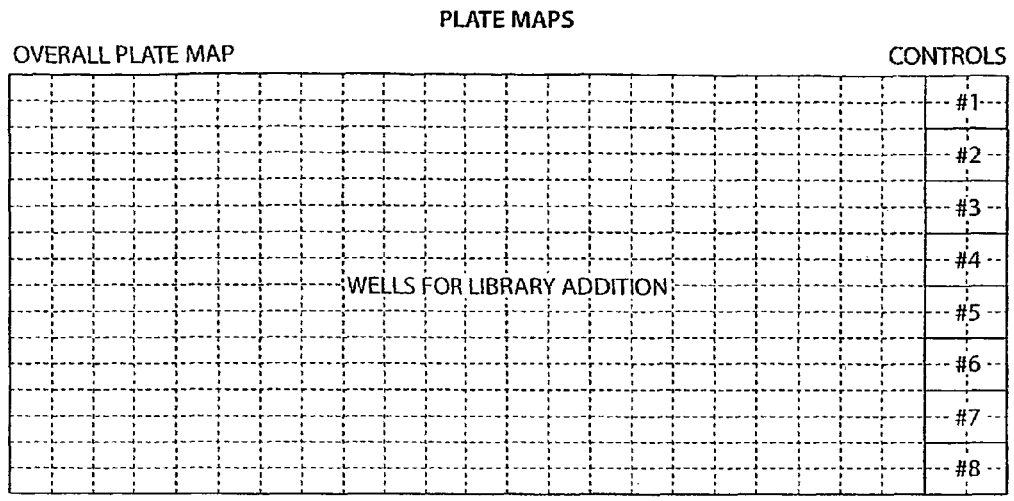
FIG. 6 illustrates schematically a 384 well plate and indicates the control wells.
Figure 7:
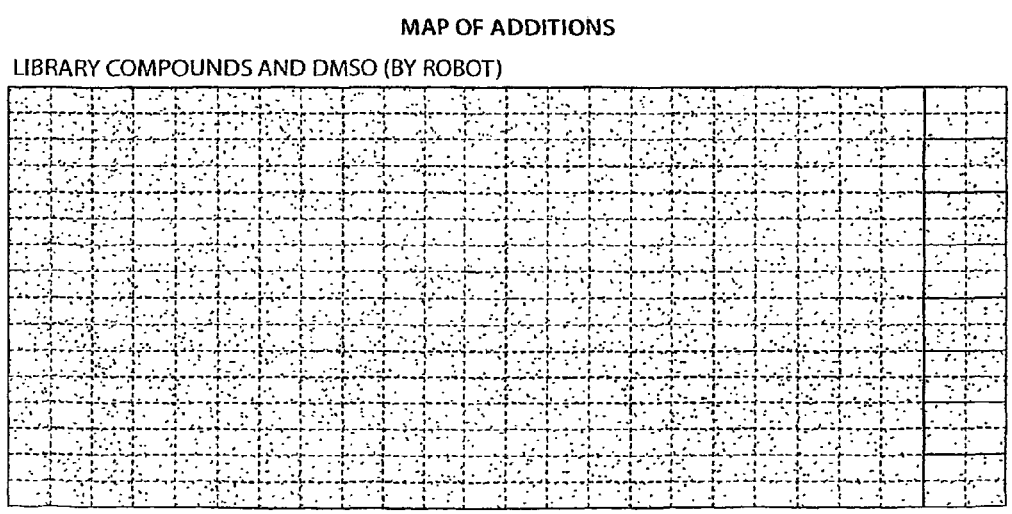
FIG. 7 illustrates schematically a 384 well plate and indicates the wells to which library compounds were added.
Figure 8:
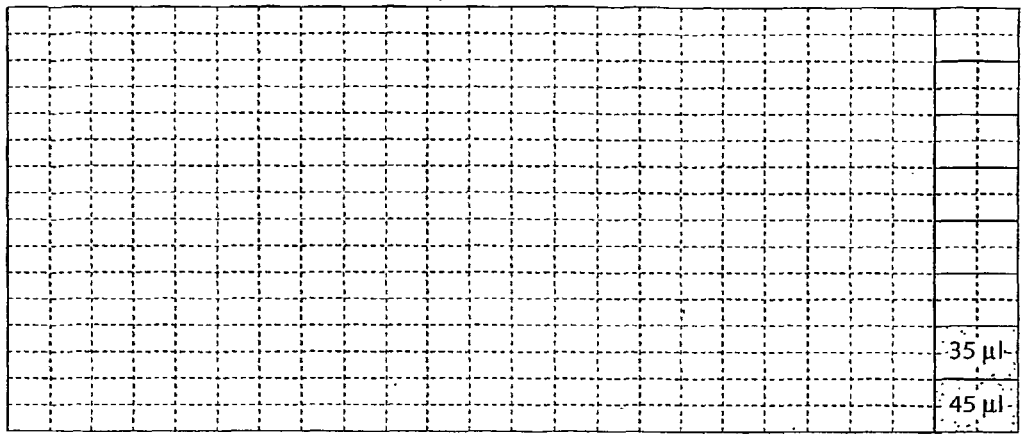
FIG. 8 illustrates schematically a 384 well plate and indicates the wells to which citrate buffer were added.
Figure 9:
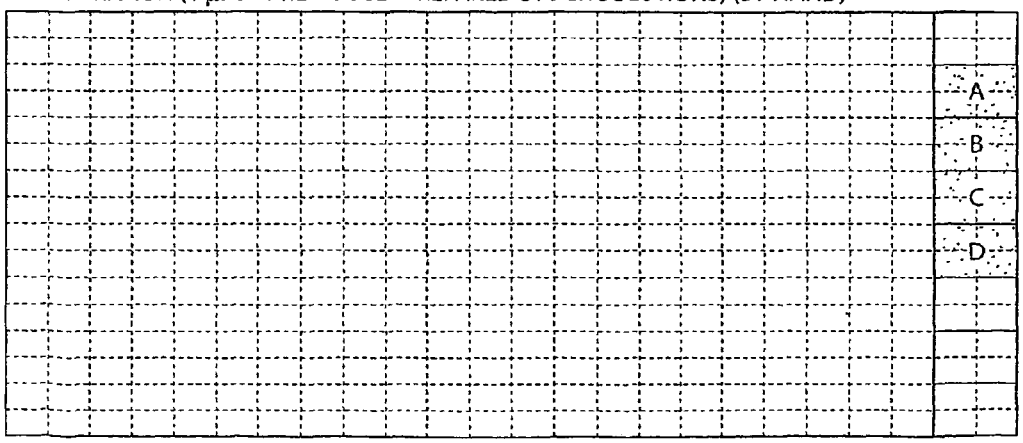
FIG. 9 illustrates schematically a 384 well plate and indicates the wells to which 35 μl of 105 nM HLA-DR2b were added.
Figure 10:
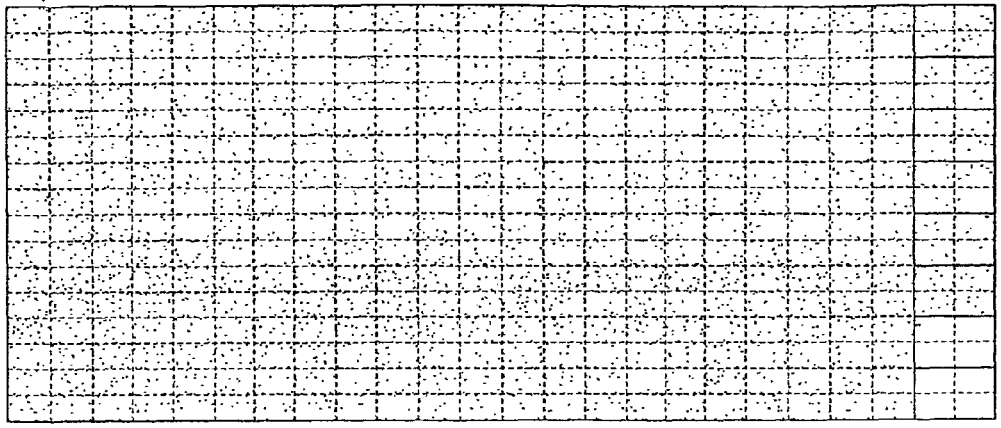
FIG. 10 illustrates schematically a 384 well plate and indicates the wells to which 1 μl MBP 85-99 was added.
Figure 11:
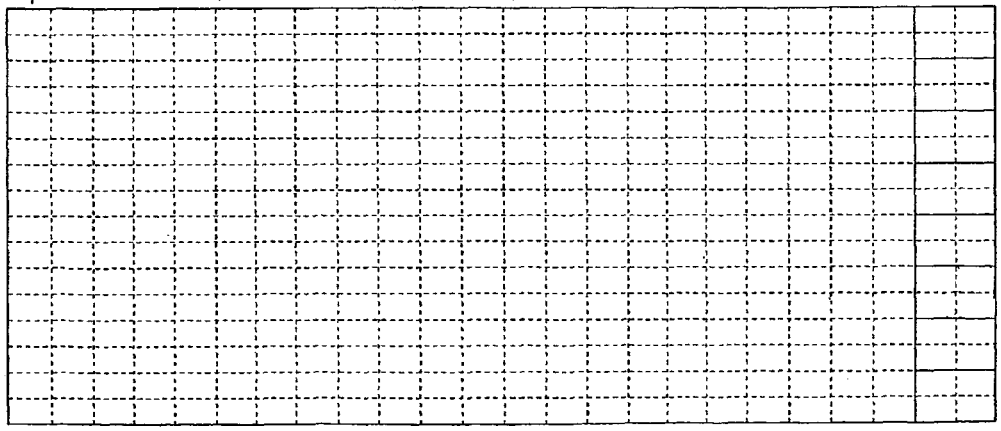
FIG. 11 illustrates schematically a 384 well plate and indicates the wells to which 5 μl MBP 85-99 was added.
Figure 12:
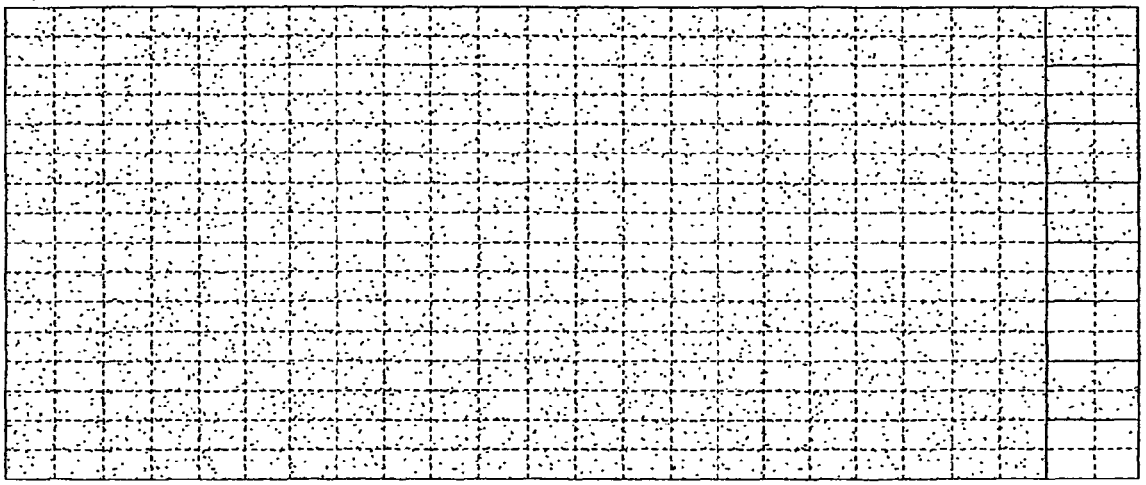
FIG. 12 illustrates schematically a 384 well plate and indicates the wells to which 5 μl of a MBP/DM mix were added.

Stock Solutions:
MBP (unlabeled) stock solutions (3.7 µM, 1.2 µM, 412 nM, 137 nM)
MBP (Alexa 488 at P5): 80 nM in 50 mM Citrate pH5.2/150 mM NaCl.
All controls in 50 mM Citrate pH5.2/150 mM NaCl buffer
Controls 1-8 were added to wells as indicated in FIG. 6.

Control #1: No Library Compound
100 nM HLA-DR2b
100 nM HLA-DM
10 nM MBP (Alexa 488 at P5)
1.0% DMSO Control #2: Cold MBP Titration A
100 nM FILA-DR2b
100 nM HLA-DM
10 nM MBP (Alexa 488 at P5)
93 nM MBP (unlabeled) (1 µl of 3.7 µM MBP (unlabeled) stock solution)
1.0% DMSO Control #3: Cold MBP Titration B
100 nM HLA-DR2b
100 nM HLA-DM
10 nM MBP (Alexa 488 at P5)
31 nM MBP (unlabelled) (1 µl of 1.2 µM MBP (unlabeled) stock solution)
1.0% DMSO Control #4: Cold MBP Titration C
100 nM HLA-DR2b
100 nM HLA-DM
10 nM MBP (Alexa 488 at P5)
10 nM MBP (unlabeled) (1 µl of 412 nM MBP (unlabeled) stock solution)
1.0% DMSO Control #5: Cold MBP Titration D 100 nM HLA-DR2b
100 nM HLA-DM
10 nM MBP (Alexa 488 at P5)
3 nM MBP (unlabeled) (1 μl of 137 nM MBP (unlabeled) stock solution)
1.0% DMSO
Control #6: No HLA-DM Control
100 nM HLA-DR2b
10 nM MBP (Alexa 488 at P5) (9 μl of 44 nM MBP (Alexa 488) stock solution)
1.0% DMSO
Control #7: No HLA-DR2b Control
100 nM HLA-DM
10 nM MBP (Alexa 488 at P5)
1.0% DMSO
Control #8: Background Control
1.0% DMSO in buffer Protocol 1. Add 0.4 μl of library compound in 100% DMSO to wells (see FIG. 7) containing HLA-DR2b. (Library compounds at 50 mM). Also add 0.4 μl DMSO to all control wells during this step. This step can be carried out days before screening commences.
2. Add 35 μl of 50 mM Citrate pH5.2/150 mM NaCl buffer to wells M23, M34, N23 and N24. See FIG. 8.
3. Add 40 μl of 50 mM Citrate pH 5.2/150 mM NaCl buffer to wells O23, O24, P23 and P24. See FIG. 8.
4. Add 35 μl of 114 nM HLA-DR2b in 50 mM Citrate pH 5.2/150 mM NaCl buffer to appropriate wells in 384 well plate as shown below in FIG. 9. Make 114 nM HLA-DR2b solution fresh and keep cold until just before addition of library compounds
5. By hand add 1 μl of MBP 85-99 (unlabeled) titration to control wells as described below in FIG. 10.
6. Mix HLA-DR2b and compound by shaking with plate shaker for 1 minute.
7. Incubate HLA-DR2b and compound for 30 minutes at room temperature.
8. By hand add 5 μl of 80 nM MBP 85-99 (Alexa 488 at P5 position) to control wells (FIG. 11) as described below while plate is incubating at room temperature.
9. During 30 minute incubation read plates for Fluorescent Intensity using the Analyst (Molecular Devices) Parameters described below. This step is optional if Fluorescent Intensity references have already been read for the compounds being screened.
10. Add 5 p. 1 of MBP/DM mix (80 nM MBP 85-99 (Alexa 488 at P5 position)/800 nM HLA-DM in 50 mM Citrate pH 5.2/150 mM NaCl buffer) to begin reaction. See FIG. 12. Mix reaction on plate shaker for 1 minute.
11. Incubate plates at room temperature for 30 mins.
12. Read using the Analyst using the Parameters described below for Fluorescence Polarization.
13. Incubate plates at room temperature for a further 1.5 hours then read the Fluorescence Polarization.
14. Measure Fluorescence Polarization at 6 hours to obtain a final equilibrium reading.
15. Measure total Fluorescence Intensity of the wells to provide control data when data is being analyzed.

Analyst Method Parameters

| General Analyst Method Conditions (Fluorescent Polarisation) | |
|---|---|
| Method ID: | Alexa488 |
| Microplate format: | Corning Costar 384 PS |
| Excitation side: | Top |
| Emission side: | Top |
| Lamp: | Continuous |
| Readings per well: | 2 |
| Time between readings: | 100 ms |
| Integration time: | 103125 us |
| Attenuator mode: | Out |
| Z Height: | 2 mm |
| Excitation filter: | 1 Fluorescein 485 nm |
| Emission filter: | 1 Fluorescein 530 nm |
| Beamsplitter: | Top Fluorescein 505 |
| Excitation polarizer filter: | S |
| Emission polarizer filter: | S |
| Detector counting: | SmartRead |
| Sensitivity setting: | 1 |

| General Analyst Method Conditions (Fluorescent Intensity) | |
|---|---|
| Method ID: | Alexa488 |
| Microplate format: | Corning Costar 384 PS |
| Excitation side: | Top |
| Emission side: | Top |
| Lamp: | Continuous |
| Readings per well: | 5 |
| Time between readings: | 100 ms |
| Integration time: | 100000 us |
| Attenuator mode: | out |
| Z Height: | 2 mm |
| Excitation filter: | 1 Fluorescein 485 nm |
| Emission filter: | 1 Fluorescein 530 nm |
| Beamsplitter: | Top Fluorescein 505 |
| Excitation polarizer filter: | out |
| Emission polarizer filter: | out |
| Detector counting: | SmartRead plus |
| Sensitivity setting: | 1 |

Examples Showing Compound Results

FIG. 1 illustrates the Fluorescent Polarization (FP) recorded at various concentrations of DR2b for a sample containing 10 nM MBP peptide in the presence of HLA-DM. The FP reading provides an indication of the amount of MBP that is bound to DR2b. FP was recorded after samples had been incubated overnight at 37° C. As the concentration of DR2b increased, the FP increased, indicating a greater amount of binding of the labeled MBP. Using widely varying concentrations of DR2b, the results provide minimum (little or no binding) and maximim (maximum binding) FP values for a 10 nM MBP peptide solution.

Figure 2:
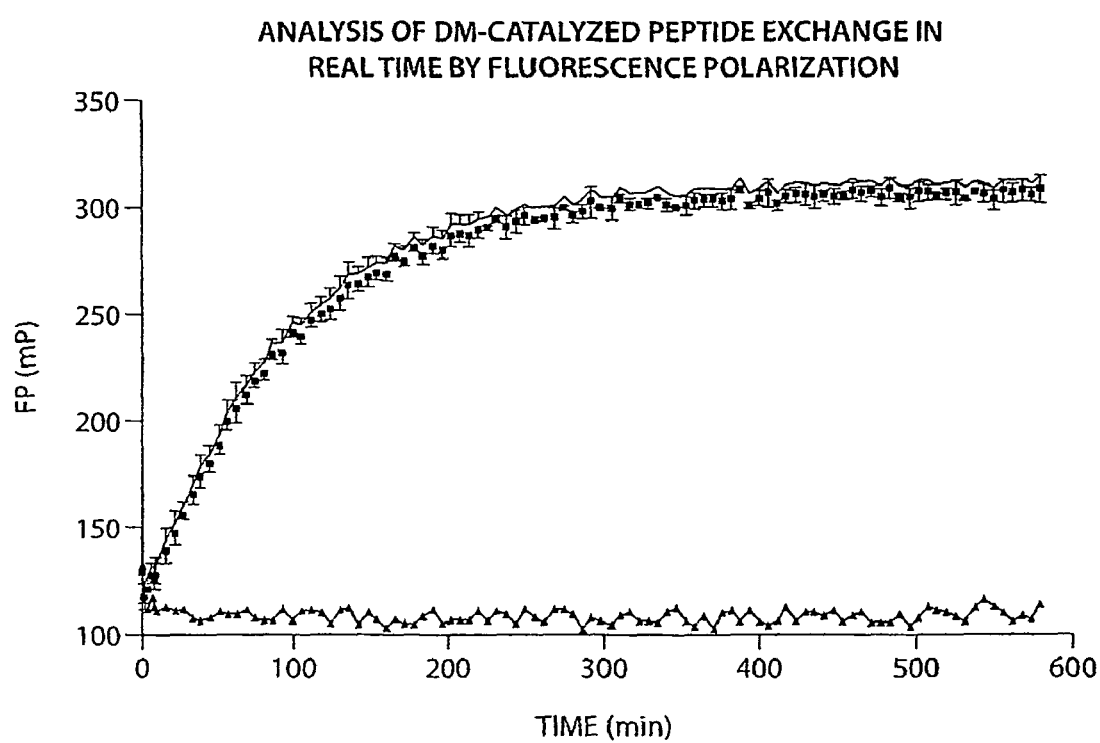
FIG. 2 graphically illustrates Fluorescence Polarization (FP) response at three different time intervals, indicating increased binding of MBP (85-89) to HLA-DR2 over a six hour period.

FIG. 2 illustrates results from a temporal study in which fluorescent readings were recorded over time. Readings were taken at 0.5 hour, 2 hours and 6 hours. The lower curve represents readings recorded for a control. The upper curve provides results for MBP binding with DR2b in the presence of HLA-DM. These data form a baseline that was used to evaluate the effect of test library compounds on the binding reaction.

Figure 3:
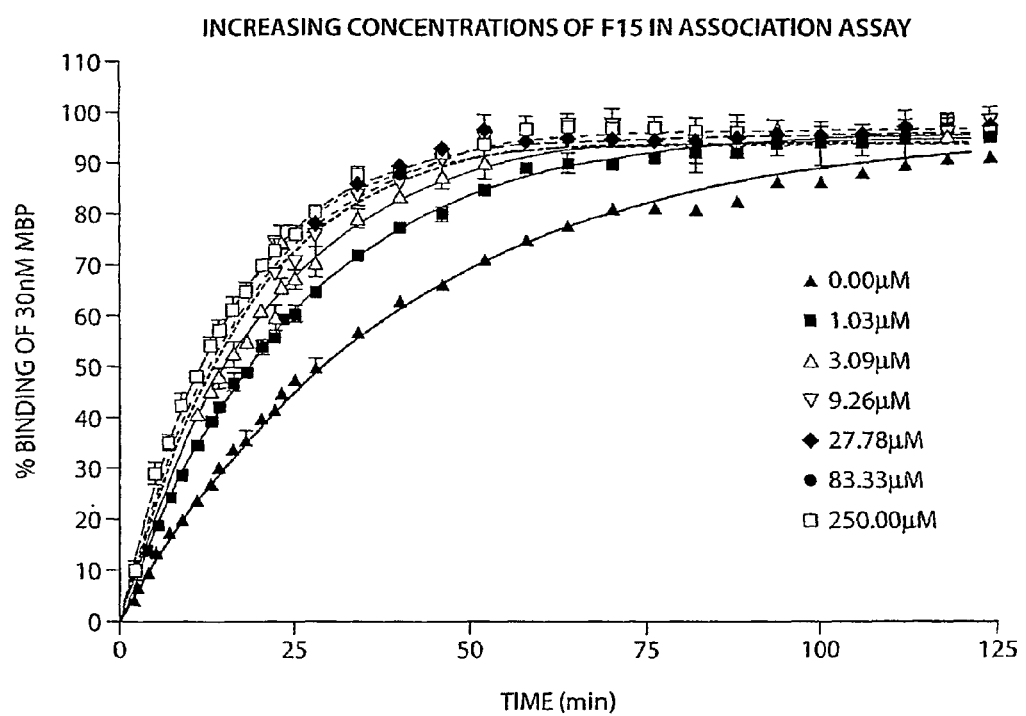
FIG. 3 graphically illustrates FP response over time for MBP/HLA-DR2 binding at seven different concentrations of F 15.

FIG. 3 illustrates graphically the effect of various concentrations of F15 in the association assay. The results indicate a significant increase in the rate of peptide exchange in the presence of F15 at concentrations as low as 1 μM. For instance, compound F15 provided for accelerated binding with an increase of about 25% at the 30 minute sampling time when compared to the control. As gains in FP (and thus peptide exchange) were made early in the assay, eg, at about 30 minutes or less, little or no difference is measured at the 6 hour mark as most or all of the peptide exchange occurred prior to this time. Thus, the total amount of exchange over a 6 hour period was about equal between F15 and the control, but with the addition of F15 the exchange occurred at an accelerated rate, resulting in a faster peptide transfer at the MHC class II molecule. It is believed, therefore, that administration of, for example, F15 or other compounds described herein may result in improved CD4 T cell response.

Figure 4:
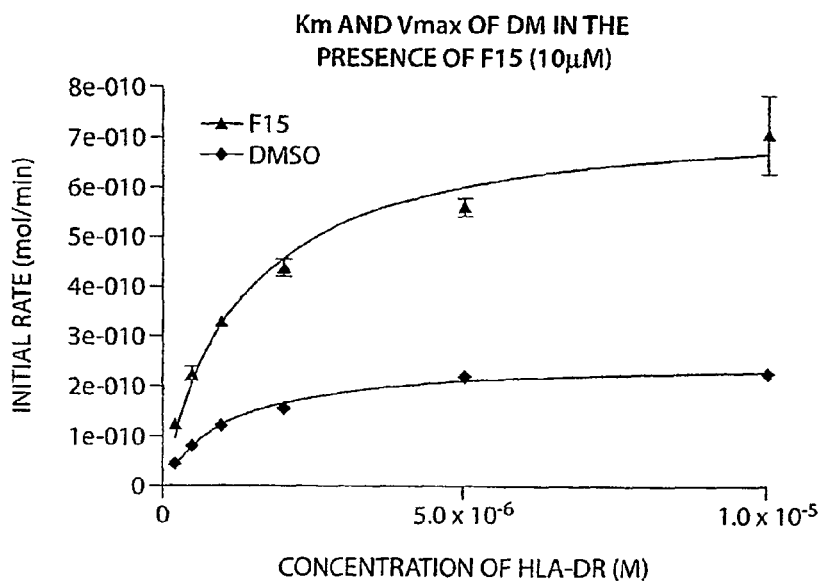
FIG. 4 graphically illustrates the effect on initial velocity of binding for MBP/HLA-DR2 in the presence of HLA-DM at different levels of HLA-DR2 with and without compound F15 present.

FIG. 4 provides results showing the acceleration of peptide exchange achieved with compound F15 at increasing levels of DR2b. The $V_{max}$ for the control was 0.02521 and was 0.07611 with F15 present at a concentration of 10 uM. Therefore, at this concentration, peptide exchange was acclerated by a factor of 3 over the control.

Figure 5A:
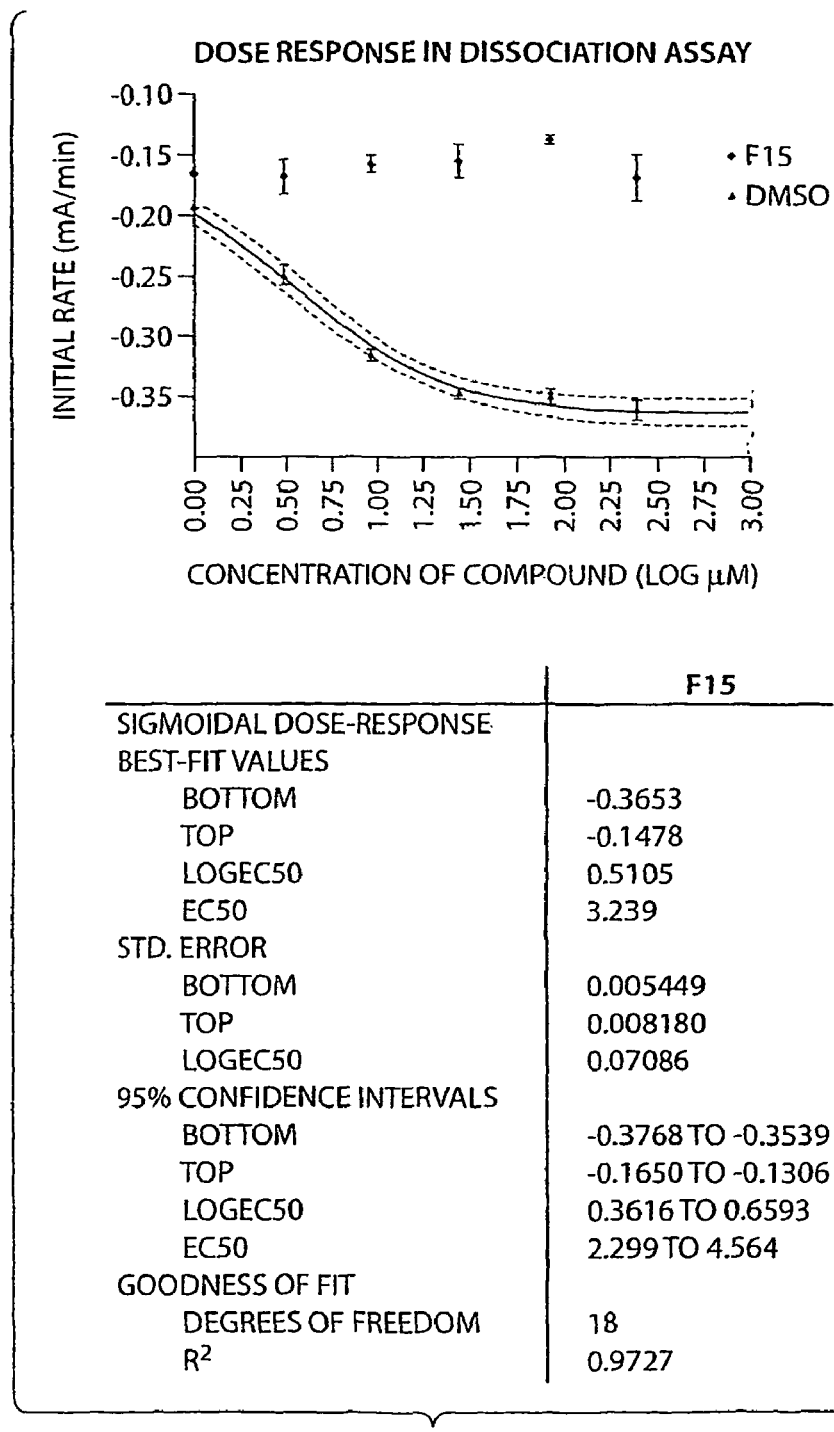
FIG. 5a graphically illustrates the results of an association assay of MBP peptide binding to HLA-DR2 in the presence of HLA-DM with compound F15 and DMSO.
Figure 5B:
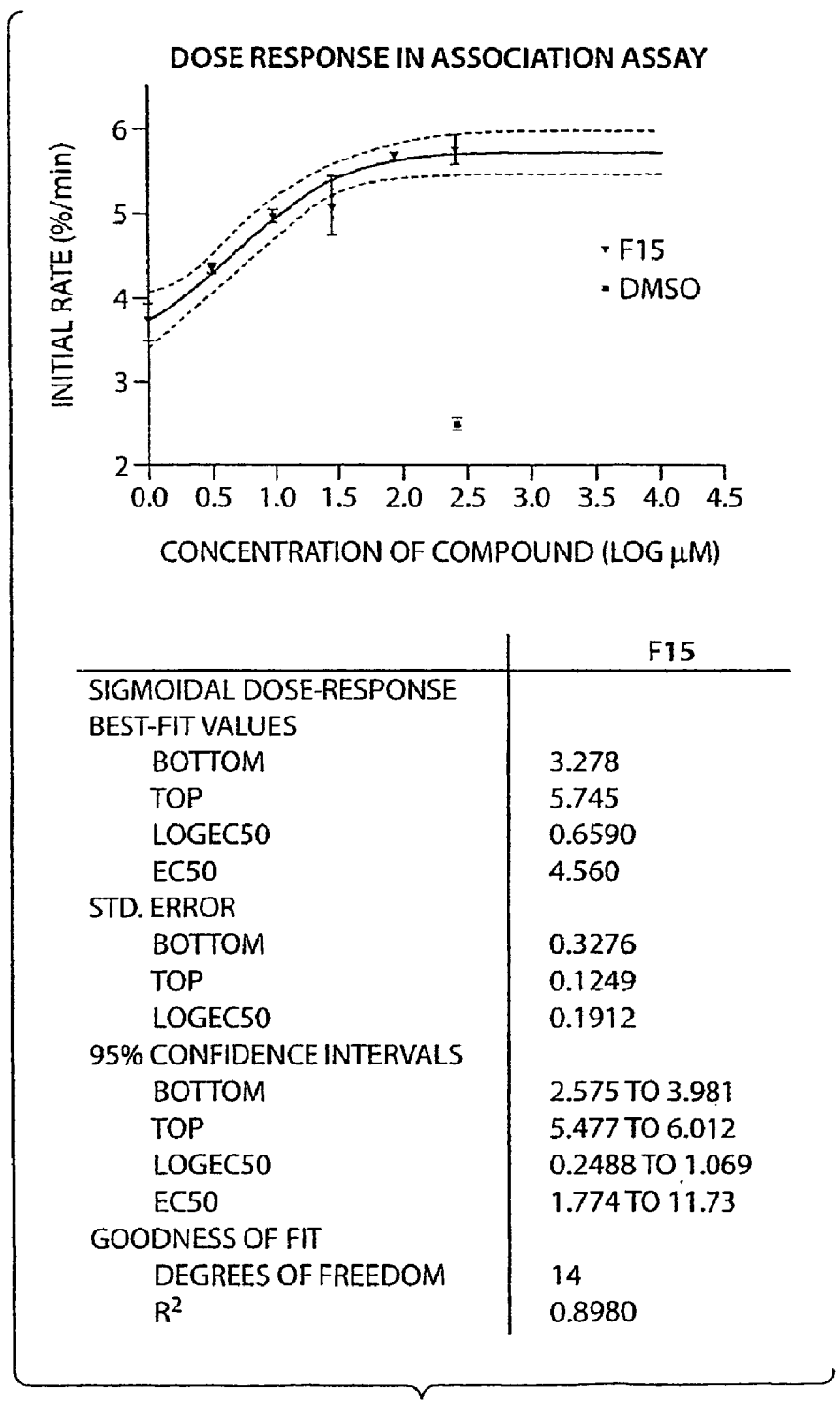
FIG. 5b illustrates graphically a dissociation assay of MBP peptide dissociating from HLA-DR2 in the presence of HLA-DM and 100-fold excess unlabeled MBP in the peptide for both F15 and DMSO.

FIGS. 5a and 5b graphically illustrate the dose reponse curve for compound F15 for disassociation (5a) and association (5b) assays. Both curves indicate a substantial effect even at very low concentrations.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of modulating an immune response in a subject, comprising:
administering to a subject in need of such immune modulation an amount of a compound effective to enhance the subject's immune response to an antigen, wherein the compound is of the formula:

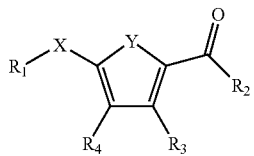

wherein,
$R_1$ is cycloalkyl;
$R_2$ is H, OH, alkyl, $OR_3$, or $N(R_3)_2$;
$R_3$ is, optionally substituted phenyl;
$R_4$ is H, CN, halogen, $CF_3$, $CO_2R_3$, or $C(O)N(R_3)_2$;
X is S, $SO_2$, O, or $NR_3$; and
Y is S, O, or $NR_3$.

2. The method of claim 1 wherein the subject is a subject having or at risk of having a cancer expressing a cancer antigen.

3. The method of claim 1 wherein the subject is a subject having or at risk of having an infectious disease.

4. A method of enhancing MHC Class II catalyzed peptide exchange comprising contacting a cell bearing a MHC Class II molecule with a compound in the presence of a peptide that binds MHC class II, wherein the compound is of the formula:

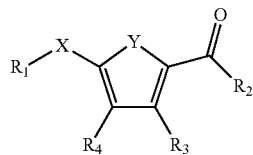

wherein,
$R_1$ is cycloalkyl;
$R_2$ is H, OH, alkyl, $OR_3$, or $N(R_3)_2$;
$R_3$ is, optionally substituted phenyl;
$R_4$ is H, CN, halogen, $CF_3$, $CO_2R_3$, or $C(O)N(R_3)_2$;
X is S, $SO_2$, O, or $NR_3$; and
Y is S, O, or $NR_3$.

5. The method of claim 1, wherein
$R_1$ is cycloalkyl;
$R_2$ is H, OH, $OR_3$, or $N(R_3)_2$;
$R_3$ is optionally substituted phenyl;
$R_4$ is H, CN, halogen, $CF_3$, or $C(O)N(R_3)_2$;
X is S, $SO_2$, or O; and
Y is S or O.

6. The method of claim 1, wherein
$R_1$ is cycloalkyl;
$R_2$ is H, OH, $OR_3$, or $N(R_3)_2$;
$R_3$ is, optionally substituted phenyl;
$R_4$ is H, CN, F, Cl, Br, or $CF_3$;
X is S; and
Y is S.

7. The method of claim 1, wherein the compound is represented by the formula:

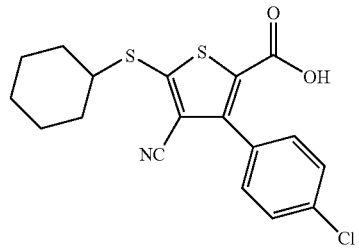

8. The method of claim 1, further comprising administering an antigen to the subject.

9. The method of claim 8, wherein the antigen is a cancer antigen.

10. The method of claim 8, wherein the antigen is a viral antigen, a bacterial antigen, a fungal antigen or a parasitic antigen.

11. The method of claim 4, wherein
$R_1$ is cycloalkyl;
$R_2$ is H, OH, $OR_3$, or $N(R_3)_2$;
$R_3$ is, optionally substituted phenyl;
$R_4$ is H, CN, halogen, $CF_3$, or $C(O)N(R_3)_2$;
X is S, $SO_2$, or O; and
Y is S or O.

12. The method of claim 4, wherein
$R_1$ is cycloalkyl;
$R_2$ is H, OH, $OR_3$, or $N(R_3)_2$;
$R_3$ is, optionally substituted phenyl;
$R_4$ is H, CN, F, Cl, Br, or $CF_3$;
X is S; and
Y is S.

13. The method of claim 4, wherein the compound is represented by the formula:
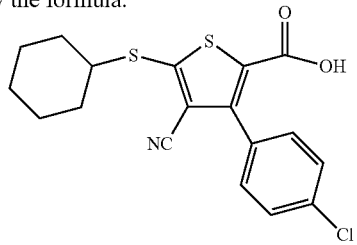
14. The method of claim 4, further comprising contacting the cell with an antigen.
15. The method of claim 14, wherein the antigen is a cancer antigen.
16. The method of claim 14, wherein the antigen is a viral antigen, a bacterial antigen, a fungal antigen or a parasitic antigen.
* * * * *